(12) United States Patent
Goletz et al.

(10) Patent No.: US 9,051,370 B2
(45) Date of Patent: Jun. 9, 2015

(54) HUMANIZED EGFR ANTIBODIES

(75) Inventors: Steffen Goletz, Berlin (DE); Antje Danielczyk, Berlin (DE)

(73) Assignee: Glycotope GmbH, Berlin (DE)

( * ) Notice: Subject to any disclaimer, the term of this patent is extended or adjusted under 35 U.S.C. 154(b) by 84 days.

(21) Appl. No.: 13/814,779

(22) PCT Filed: Aug. 10, 2011

(86) PCT No.: PCT/EP2011/063781
§ 371 (c)(1),
(2), (4) Date: Feb. 7, 2013

(87) PCT Pub. No.: WO2012/020059
PCT Pub. Date: Feb. 16, 2012

(65) Prior Publication Data
US 2013/0273033 A1   Oct. 17, 2013

Related U.S. Application Data

(60) Provisional application No. 61/372,186, filed on Aug. 10, 2010.

(30) Foreign Application Priority Data

Aug. 10, 2010 (EP) ..................... 10008319

(51) Int. Cl.
  A61K 39/395   (2006.01)
  C07K 16/28    (2006.01)
  C12N 5/10     (2006.01)
  C12N 15/11    (2006.01)

(52) U.S. Cl.
  CPC ......... C07K 16/2863 (2013.01); *C07K 2317/24* (2013.01); *C07K 2317/565* (2013.01); *C07K 2317/567* (2013.01)

(58) Field of Classification Search
  None
  See application file for complete search history.

(56) References Cited

U.S. PATENT DOCUMENTS

| 5,859,205 | A * | 1/1999 | Adair et al. |
| 7,723,484 | B2 * | 5/2010 | Beidler et al. |
| 8,658,175 | B2 * | 2/2014 | Dubridge et al. |
| 2005/0084906 | A1 | 4/2005 | Goetsch et al. |
| 2010/0056762 | A1 | 3/2010 | Old |

FOREIGN PATENT DOCUMENTS

| WO | WO 9640210 A1 * | 12/1996 |
| WO | 2008/028686 A2 | 3/2008 |
| WO | 2012/020065 A1 | 2/2012 |

OTHER PUBLICATIONS

Sela-Culang, et al., The Structural Basis of Antibody-Antigen Recognition. Frontiers in immunology, vol. 4, article 302, pp. 1-13, Oct. 2013.*

(Continued)

*Primary Examiner* — Claire Kaufman
(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to humanized anti-EGFR antibodies having antigen binding properties similar to those of the murine or chimeric anti-EGFR antibody from which they are derived. In particular, the present invention is directed to humanized anti-EGFR antibodies which are useful in the treatment of cancer.

19 Claims, 14 Drawing Sheets

(56) References Cited

OTHER PUBLICATIONS

Pascalis, et al., Grafting of "abbreviated" complementarity-determining regions containing specificity-determining residues essential for ligand contact to engineer a less immunogenic humanized monoclonal antibody. J. Immunol., 169(6):3076-3084, Sep. 15, 2002.*

Kabat, E.A. et al., NTIS Accession No. PB91-192898, Sequences of Proteins of Immunological Interest, vol. 1, 2, and 3, Fifth Edition, 1 page (1991), Abstract only.

Liu, Xiao-yun et al., "Engineering therapeutic monoclonal antibodies," Immunological Reviews, vol. 222:9-27 (2008).

Presta, Leonard G., "Engineering of therapeutic antibodies to minimize immunogenicity and optimize function," Advanced Drug Delivery Reviews, vol. 58:640-656 (2006).

International Preliminary Report on Patentability and Written Opinion for Application No. PCT/EP2011/063781, 5 pages, dated Feb. 12, 2013.

International Search Report for Application No. PCT/EP2011/063781, 4 pages, dated Nov. 18, 2011.

* cited by examiner

A

B

HUMANIZED EGFR ANTIBODIES

FIELD OF THE INVENTION

The present invention pertains to the field of antibodies. In particular, a humanized anti-EGFR antibody showing an improved antigen binding and/or recognition is provided. In specific embodiments, the present invention is directed to humanized anti-EGFR antibodies which are useful in the treatment of cancer.

BACKGROUND OF THE INVENTION

Today, antibodies are widely used agents in the field of medicine and research. In medicine, they find application in many different fields. For example, antibodies are used as labeling agents for detecting certain markers which allow the diagnosis and/or prognosis of diseases or the determination of specific body parameters such as, for example, the presence or concentration of certain hormones.

Furthermore, antibodies are also used as therapeutic agents in the treatment and prophylaxis of a variety of diseases such as cancer, cardiovascular diseases, inflammatory diseases, macular degeneration, transplant rejection, multiple sclerosis, and viral infections. In these therapies, the antibody may possess therapeutic activity on it own, for example by blocking receptors or messenger molecules, thereby inhibiting their disease-relevant functions, or by recruiting and activating components of the patient's immune system. Alternatively, the antibody may be coupled to another agent having therapeutic activity. In particular in the treatment of cancer and infections, said further agent has cell-killing activity and may be, for example a radioisotope or a cytotoxin. In another application, antibodies may be used to passively immunize a patient by transferring suitable antibodies into the patient's circulation.

Specific antibodies are produced by injecting an antigen into a mammal, such as a mouse, rat, rabbit, goat, sheep, or horse. Blood isolated from these animals contains polyclonal antibodies directed against said antigen in the serum. To obtain an antibody that is specific for a single epitope of an antigen, antibody-secreting lymphocytes are isolated from the animal and immortalized by fusing them with a cancer cell line, resulting in hybridoma cells. Single hybridoma cells are then isolated by dilution cloning to generate cell clones that all produce the same monoclonal antibody.

However, in therapeutic applications these monoclonal antibodies have the problem that they are derived from animal organisms and differ in their amino acid sequence from human antibodies. The human immune system hence recognizes these animal antibodies as foreign and rapidly removes them from circulation. Furthermore, systemic inflammatory effects may be caused. A solution to this problem is the replacement of certain constant parts of the monoclonal antibody with corresponding parts of a human antibody. If only the heavy and light chain constant regions are replaced, a chimeric antibody is obtained, while the additional replacement of the framework regions of the heavy and light chain variable regions results in so called humanized antibodies.

In research, purified antibodies are used in many applications. They are most commonly used to identify and locate biological molecules such as in particular proteins. The biological molecules may either be detected after they have been isolated, for example to determine their presence, concentration, integrity or size. On the other hand, they may be detected in cellular or tissue samples, for example to determine their presence or location. Furthermore, antibodies are used in isolation procedures of specific biological substances, in particular proteins, wherein the antibody specifically separates the biological substance of interest from the sample containing it.

In all these applications, a tight binding and specific recognition of the antigen is of vital importance for the antibody used. Thereby, higher activity and less cross-reactivity, in particular less adverse side effects in therapeutic applications, are obtained. However, during humanization of monoclonal antibodies, often the affinity and specificity of the engineered antibody is decreased.

An interesting and important group of antibodies are those directed against epidermal growth factor receptors (EGFR). The EGF receptor is a receptor tyrosine kinase which is anchored in the plasma membrane. The extracellular domain binds to epidermal growth factor which results in dimerization of the receptor and stimulation of its intracellular protein-tyrosine kinase activity. The signal transduction cascades initiated by the active receptor dimer control cell migration, adhesion, and proliferation.

Overexpression of EGFR or overactivity has been found in a number of cancers, including lung cancer, anal cancers, and glioblastomas. Mutations, amplifications or misregulations of EGFR or family members are implicated in about 30% of all epithelial cancers and are associated with a poor prognosis.

Antibodies, especially monoclonal antibodies, raised against EGFR have been established as anti-tumor agents. Such antibodies may compete with the EGFR ligands such as EGF and TGFα in binding to the receptors, thereby inhibiting the growth of tumors that express the receptor. Furthermore, the antibodies may inhibit the growth of tumors immunologically through antibody-dependent cellular cytotoxicity (ADCC) or complement-dependent cytotoxicity (CDC). In another approach, toxins are conjugated to the antibodies. The antibody portion directs the conjugate to the tumor, which is then killed by the toxin portion.

Several antibodies directed against EGFR are known in the art. Some of them are already approved for medical applications. However, a disadvantage of using murine monoclonal antibodies in human therapy is the possibility of a human anti-mouse antibody (HAMA) response due to the presence of mouse Ig sequences. This disadvantage can be minimized by replacing the entire constant region of a murine (or other non-human mammalian) antibody with that of a human constant region (chimerization). The chimerization process can be made more effective by also replacing the framework regions of the variable regions of a murine antibody with the corresponding human sequences (humanization). The humanized antibody is less immunogenic (i.e. elicits less of a HAMA response) as more murine sequences are replaced by human sequences.

Unfortunately, a humanized antibody often has a lower affinity and specificity for its target antigen than the corresponding non-human or chimeric antibody. This, as the overall three-dimensional structure of the variable regions and in particular the conformation and orientation of the complementarity determining regions (CDRs) may be altered by the replacement of the framework regions.

Therefore, there is a need in the art to provide humanized antibodies, in particular humanized anti-EGFR antibodies, in particular humanized versions of Cetuximab, which have an antigen binding affinity and antigen specificity similar to that of the corresponding murine or chimeric antibody.

SUMMARY OF THE INVENTION

The present inventors have found humanized epidermal growth factor receptor (EGFR) antibodies having the same antigen binding affinity and circulation half-life as the parent chimeric antibody from which they are derived.

Therefore, in a first aspect, the present invention is directed to a humanized antibody or a fragment or derivative thereof which is capable of binding to EGFR and which comprises a heavy chain variable region, wherein the CDR1 has the amino acid sequence of SEQ ID NO: 1, the CDR2 has the amino acid sequence of SEQ ID NO: 2, and the CDR3 has the amino acid sequence of SEQ ID NO: 3, and wherein one or more of the framework regions 1, 2 and 3 are derived from or correspond to the corresponding framework region of a heavy chain variable region amino acid sequence comprising SEQ ID NO: 31.

In a second aspect, the present invention provides a nucleic acid encoding the antibody or fragment or derivative thereof according to the invention. Furthermore, in a third aspect an expression cassette or vector comprising the nucleic acid according to the invention and a promoter operatively connected with said nucleic acid and, in a fourth aspect, a host cell comprising the nucleic acid or the expression cassette or vector according to the invention are provided.

In a fifth aspect, the present invention provides a conjugate comprising the antibody or fragment or derivate thereof according to the invention conjugated to a detectable marker or a therapeutically active substance.

In a sixth aspect, the present invention is directed to a composition comprising the antibody or fragment or derivative thereof according to the invention, the nucleic acid according to the invention, the expression cassette or vector according to the invention, the host cell according to the invention, or the conjugate according to the invention.

According to a seventh aspect, the invention provides the antibody or fragment or derivative thereof, the nucleic acid, the expression cassette or vector, the host cell, the composition according to the invention, or the conjugate according to the invention for use in medicine, in particular in the treatment, prognosis, diagnosis and/or monitoring of cancer.

It was demonstrated by the inventors that the humanized antibodies according to the present invention have antibody binding properties similar to that of the chimeric antibody. This is in particular also true for the versions of the humanized antibody which lack the Fab glycosylation site of the chimeric version. This is highly surprising as the Fab glycosylation was expected to play a role in antigen binding and removal thereof would significantly impair antigen binding. Furthermore, binding to the downstream Fcγ IIIA receptor and the ADCC, tumor cell lysis and tumor growth inhibition activities of the humanized antibodies are also comparable to the chimeric version. In addition, it could be demonstrated that the circulation half-life in mice is highly similar for the chimeric and the humanized version. As the antibody's clearance rate in humans will benefit from humanization, the humanized antibody will have a longer circulation half-life in humans. It can also be expected that the concentration of the therapeutic antibody at the target site (e.g. the tumor) is higher for the humanized version when equal doses are administered. Therefore, the therapeutic efficacy of the humanized antibody according to the present invention is superior to that of the chimeric antibody. Therefore, the humanized antibodies according to the present invention may be administered in lower doses and/or less frequently than the chimeric antibody.

Furthermore, the present inventors could demonstrate that the sialylation degree at the Fab part of an antibody comprising a Fab glycosylation site significantly influences the circulation half-life of the antibody. A higher sialylation degree results in a higher circulation half-life, in particular in the human body. Furthermore, a corresponding antibody not having a glycosylation site in the Fab part has a circulation half-life similar to a Fab-glycosylated antibody having a high sialylation degree (see Example 4, below, and patent application filed by the applicant on Aug. 10, 2011 entitled "Fab-Glycosylated Antibodies", priority application PCT/EP2010/004878). This is contrary to the teaching in the prior art. The present inventors surprisingly found that the humanized antibody according to the present invention which does not comprise a glycosylation site in its Fab part due to the performed humanization has a high circulation half-life which is independent of its glycosylation pattern and thus, is independent of the cell line that is used for its production. This is an important advantage as a high circulation half-life can be achieved in primates, in particular in humans. In particular, many antibodies are produced in cell lines which have a rather low sialylation activity, such as CHO cells and SP2/0 cells, resulting in antibodies having a low degree of sialylation. The humanized antibody according to the present invention which does not have a Fab glycosylation site due to the performed humanization can be produced in these cell lines without the disadvantage of a low circulation half-life. Therefore, the removal of the glycosylation site in the Fab part of the antibody is highly advantageous for the humanized antibody according to the present invention.

The humanized antibodies according to the present invention, as well as the fragments, derivatives or conjugates thereof, have the further advantage that they cause only very few or no adverse effects when administered to humans, in particular only very few or no severe adverse effects. Especially, they cause less (severe) adverse effects than their chimeric or mouse counterparts. Particularly no HAMA response will occur when using the antibodies, fragments, derivatives or conjugates according to the present invention.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DEFINITIONS

As used herein, the following expressions are generally intended to preferably have the meanings as set forth below, except to the extent that the context in which they are used indicates otherwise.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The term "antibody" particularly refers to a protein comprising at least two heavy chains and two light chains connected by disulfide bonds. The term "antibody" includes naturally occurring antibodies as well as all recombinant forms of antibodies, e.g., antibodies expressed in prokaryotes, unglycosylated antibodies, humanized antibody, and chimeric antibody. Each heavy chain is comprised of a heavy chain variable region (VH) and a heavy chain constant region (CH). Each light chain is comprised of a light chain variable region (VL) and a light chain constant region (CL). The heavy chain-constant region comprises three or—in the case of antibodies of the IgM- or IgE-type—four heavy chain-constant domains (CH1, CH2, CH3 and CH4) wherein the first constant domain CH1 is adjacent to the variable region and may be connected to the second constant domain CH2 by a hinge region. The light chain-constant region consists only of one constant domain. The variable regions can be further subdivided into regions of hypervariability, termed complementarity determining regions (CDRs), interspersed with regions that are more conserved, termed framework regions (FR), wherein each variable region comprises three CDRs and four FRs. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" according to the invention, however, also includes antibodies such as heavy chain antibodies, i.e. antibodies only composed of one or more, in particular two heavy chains, and nanobodies, i.e. antibodies only composed of a single monomeric variable domain.

For indicating the amino acid positions of the heavy chain and light chain variable regions, the Kabat numbering system is used herein (Kabat, E. A. et al. (1991) *Sequences of Proteins of Immunological Interest*, 5$^{th}$ edition, NIH Publication No. 91-3242). According to said system, the heavy chain comprises amino acid positions from position 0 to position 113 including position 35A, 35B, 52A to 52C, 82A to 82C and 100A to 100K. The CDRs of the heavy chain variable region are located, according to the Kabat numbering, at positions 31 to 35B (CDR1), 50 to 65 (CDR2) and 95 to 102 (CDR3). The remaining amino acid positions form the framework regions FR1 to FR4. The light chain variable region comprises positions 0 to 109 including positions 27A to 27F, 95A to 95F and 106A. The CDRs are located at positions 24 to 34 (CDR1), 50 to 56 (CDR2) and 89 to 97 (CDR3). Depending on the initial formation of the specific gene of an antibody, not all of these positions have to be present in a given heavy chain variable region or light chain variable region. In case an amino acid position in a heavy chain or light chain variable region is mentioned herein, unless otherwise indicated it is referred to the position according to the Kabat numbering.

According to the present invention, the term "humanized antibody" in particular refers to an antibody wherein at least one CDR is derived from a non-human antibody, and wherein the constant regions, if present, and at least one framework region of a variable region are derived from a human antibody or a human antibody consensus sequence. Preferably, all CDRs of the heavy chain variable region or, more preferably, all CDRs of the heavy chain variable region and the light chain variable region, are derived from the non-human antibody. Furthermore, preferably all framework regions of the heavy chain variable region or, more preferably, all framework regions of the heavy chain variable region and the light chain variable region, are derived from a human antibody or a human antibody consensus sequence. The CDRs preferably are derived from the same non-human antibody. The first three or all of the framework regions of one variable region preferably are derived from the same human antibody or human antibody consensus sequence, however, the framework regions of the heavy chain variable region do not have to be derived from the same human antibody or human antibody consensus sequence as the framework regions of the light chain variable region. In particular preferred embodiments, the humanized antibody is capable of binding to the same antigens, in particular the same epitopes as the non-human antibody from which the one or more CDRs are derived.

Preferably, the CDRs of the humanized antibody which are derived from the non-human antibody are identical to the CDRs of the non-human antibody. Furthermore, the framework regions of the humanized antibody which are derived from the human antibody or human antibody consensus sequence may be identical to the framework regions of the human antibody or human antibody consensus sequence. In another embodiment, the framework regions of the humanized antibody may have one or more amino acid substitutions compared to the framework regions of the human antibody or human antibody consensus sequence from which they are derived. The substituted amino acid residues are preferably replaced by the corresponding amino acid residues of the non-human antibody from which one or more of the CDRs are derived (in particular those corresponding amino acid residues which are at the same position according to the Kabat numbering). In particular, the framework regions of a variable region (heavy chain variable region and/or light chain variable region) of the humanized antibody preferably comprise no more than 30 amino acid substitutions, preferably no more than 25, no more than 20, nor more than 15, no more than 12, no more than 10 or no more than 8 amino acid substitutions.

In preferred embodiments, all framework regions of the heavy chain variable region of the humanized antibody, taken together, share a homology or an identity of at least 70%, preferably at least 75%, at least 80%, at least 85% or at least 90%, with the framework regions of the heavy chain variable region of the human antibody or human antibody consensus sequence from which they are derived. Furthermore, all framework regions of the light chain variable region of the humanized antibody, taken together, preferably share a homology or an identity of at least 70%, preferably at least 75%, at least 80%, at least 85% or at least 90%, with the framework regions of the light chain variable region of the human antibody or human antibody consensus sequence from which they are derived.

The constant regions of the humanized antibody may be derived from any human antibody or human antibody consensus sequence. In particular, the heavy chain constant regions may be of any type such as γ-, δ-, α-, μ- or ε-type heavy chains. The humanized antibody may thus be of any isotype such as IgA, IgD, IgE, IgG or IgM, including any subclass such as IgG1, IgG2, IgG3, IgG4, IgA1 or IgA2. Preferably, the humanized antibody is an IgG1- or IgG2-antibody, more preferably an IgG1-antibody. Furthermore, the light chain constant region may also be of any type such as κ- or λ-type light chains. Preferably, the light chain of the humanized antibody is a κ-chain.

A target amino acid sequence is "derived" from or "corresponds" to a reference amino acid sequence if the target amino acid sequence shares a homology or identity over its entire length with a corresponding part of the reference amino acid sequence of at least 60%, preferably at least 70%, at least 75%, more preferably at least 80%, at least 85%, at least 90%, at least 93%, at least 95% or at least 97%. For example, if a framework region of a humanized antibody is derived from or corresponds to a variable region of a particular human antibody, then the amino acid of the framework region of the humanized antibody shares a homology or identity over its entire length with the corresponding framework region of the human antibody of at least 60%, preferably at least 70%, at least 75%, more preferably at least 80%, at least 85%, at least 90%, at least 93%, at least 95% or at least 97%. The "corresponding part" or "corresponding framework region" means that, for example, framework region 1 of a heavy chain variable region (FRH1) of a target antibody corresponds to framework region 1 of the heavy chain variable region of the reference antibody. The same is true, for example, for FRH2, FRH3, FRH4, FRL1, FRL2, FRL3 and FRL4. In particular embodiments, a target amino acid sequence which is "derived" from or "corresponds" to a reference amino acid sequence is 100% homologous, or in particular 100% identical, over its entire length with a corresponding part of the reference amino acid sequence.

A "fragment or derivative" of an antibody in particular is a protein or glycoprotein which is derived from said antibody and is capable of binding to the same antigen, in particular to the same epitope as the antibody. Thus, a fragment or derivative of an antibody herein generally refers to a functional fragment or derivative. In particularly preferred embodiments, the fragment or derivative of an antibody comprises a heavy chain variable region. It has been shown that the antigen-binding function of an antibody can be performed by fragments of a full-length antibody or derivatives thereof. Examples of fragments or derivatives of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. These antibody fragments and derivatives are obtained using conventional techniques known to those with skill in the art.

"Specific binding" preferably means that an agent such as an antibody binds stronger to a target such as an epitope for which it is specific compared to the binding to another target. An agent binds stronger to a first target compared to a second target if it binds to the first target with a dissociation constant ($K_d$) which is lower than the dissociation constant for the second target. Preferably the dissociation constant for the target to which the agent binds specifically is more than 2-fold, preferably more than 5-fold, more preferably more than 10-fold, even more preferably more than 20-fold, 50-fold, 100-fold, 200-fold, 500-fold or 1000-fold lower than the dissociation constant for the target to which the agent does not bind specifically.

The term "epidermal growth factor receptor" or "EGFR" according to the present invention in particular refers to EGFR1, also known as HER1 or ErbB-1, preferably human EGFR1. The EGFR is a receptor tyrosine kinase comprising an extracellular ligand binding domain, a membrane-spanning domain and an intracellular kinase domain. Upon binding of a ligand, in particular EGF or TGFα, the EGFR dimerizes and its kinase function is activated, resulting in the autophosphorylation of several tyrosins of the intracellular domain.

According to the invention, the term "glycosylation site" in particular refers to an amino acid sequence which can specifically be recognized and glycosylated by a natural glycosylation enzyme, in particular a glycosyltransferase, preferably a naturally occurring mammalian or human glycosyltransferase. In particular, the term "glycosylation site" refers to an N-glycosylation site, comprising an asparagine residue to which the carbohydrate is or will be bound, and/or an O-glycosylation site, comprising a serine or threonine residue to which the carbohydrate is or will be bound. Preferably, the glycosylation site is an N-glycosylation site which preferably has the amino acid sequence Asn-Xaa-Ser/Thr/Cys, wherein Xaa is any amino acid residue. Preferably, Xaa is not Pro.

The term "nucleic acid" includes single-stranded and double-stranded nucleic acids and ribonucleic acids as well as deoxyribonucleic acids. It may comprise naturally occurring as well as synthetic nucleotides and can be naturally or synthetically modified, for example by methylation, 5'- and/or 3'-capping.

The term "conjugate" particularly means two or more compounds which are linked together so that at least some of the properties from each compound are retained in the conjugate. Linking may be achieved by a covalent or non-covalent bond. Preferably, the compounds of the conjugate are linked via a covalent bond. The different compounds of a conjugate may be directly bound to each other via one or more covalent bonds between atoms of the compounds. Alternatively, the compounds may be bound to each other via a linker molecule wherein the linker is covalently attached to atoms of the compounds. If the conjugate is composed of more than two compounds, then these compounds may, for example, be linked in a chain conformation, one compound attached to the next compound, or several compounds each may be attached to one central compound.

The term "expression cassette" in particular refers to a nucleic acid construct which is capable of enabling and regulating the expression of a coding nucleic acid sequence introduced therein. An expression cassette may comprise promoters, ribosome binding sites, enhancers and other control elements which regulate transcription of a gene or translation of an mRNA. The exact structure of expression cassette may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the operatively connected nucleic acid. Expression cassettes may also comprise enhancer sequences or upstream activator sequences.

According to the invention, the term "promoter" refers to a nucleic acid sequence which is located upstream (5') of the nucleic acid sequence which is to be expressed and controls expression of the sequence by providing a recognition and binding site for RNA-polymerases. The "promoter" may include further recognition and binding sites for further factors which are involved in the regulation of transcription of a gene. A promoter may control the transcription of a prokaryotic or eukaryotic gene. Furthermore, a promoter may be "inducible", i.e. initiate transcription in response to an inducing agent, or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. mammalian cells, in particular human cells, yeast cells and insect cells). Particular preference is given to mammalian cells such as cells from humans, mice, hamsters, pigs, goats, or primates. The cells may be derived from a multiplicity of tissue types and comprise primary cells and cell lines. A nucleic acid may be present in the host cell in the form of a single copy or of two or more copies and, in one embodiment, is expressed in the host cell.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

The term "cancer" according to the invention in particular comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, colrectal carcinomas, head and neck carcinomas, or metastases of the cancer types or tumors described above. The term cancer according to the invention also comprises cancer metastases.

By "tumor" is meant a group of cells or tissue that is formed by misregulated cellular proliferation. Tumors may show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and normally involves detachment of cancer cells from a primary tumor, entering the body circulation and settling down to grow within normal tissues elsewhere in the body. When tumor cells metastasize, the new tumor is called a secondary or metastatic tumor, and its cells normally resemble those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

The term "pharmaceutical composition" particularly refers to a composition suitable for administering to a human or animal, i.e., a composition containing components which are pharmaceutically acceptable. Preferably, a pharmaceutical composition comprises an active compound or a salt or pro-drug thereof together with a carrier, diluent or pharmaceutical excipient such as buffer, preservative and tonicity modifier.

DETAILED DESCRIPTION OF THE INVENTION

The present invention is based on the development of humanized anti-EGFR antibodies having antigen binding properties and a circulation half-life similar to those of the corresponding murine or chimeric antibody.

In view of these findings, the present invention provides a humanized antibody or a fragment or derivative thereof which is capable of binding to EGFR and which comprises at least a portion of a heavy chain variable region comprising a CDR1 having the amino acid sequence of SEQ ID NO: 1, a CDR2 having the amino acid sequence of SEQ ID NO: 2, and a CDR3 having the amino acid sequence of SEQ ID NO: 3.

In preferred embodiments, the portion of the heavy chain variable region comprised by the antibody or a fragment or derivative thereof according to the invention has a length of at least 70 amino acids, preferably at least 90 amino acids, at least 100 amino acids or at least 110 amino acids. More preferably, the portion of the heavy chain variable region at least comprises the CDRs 1 to 3, the entire framework regions 2 and 3 and at least a part of the framework regions 1 and 4. Most preferably, the antibody or a fragment or derivative thereof according to the invention comprises the complete heavy chain variable region.

In the first aspect of the present invention a humanized antibody or a fragment or derivative thereof is provided which is capable of binding to an epidermal growth factor receptor (EGFR) and which comprises a heavy chain variable region, wherein the CDR1 has the amino acid sequence of SEQ ID NO: 1, the CDR2 has the amino acid sequence of SEQ ID NO: 2, and the CDR3 has the amino acid sequence of SEQ ID NO: 3, and wherein one or more of the framework regions 1, 2 and 3 are derived from or correspond to the human germline VH gene 4-59*01 coding for an amino acid sequence comprising SEQ ID NO: 31.

In a preferred embodiment, the humanized antibody according to the invention further comprises a light chain variable region comprising a CDR1 having the amino acid sequence of SEQ ID NO: 5, and/or a CDR2 having the amino acid sequence of SEQ ID NO: 6, and/or a CDR3 having the amino acid sequence of SEQ ID NO: 7.

Preferably, the humanized antibody according to the invention is specific for EGFR, in particular human EGFR, preferably human EGFR1. It preferably is capable of specifically binding to the extracellular part of the EGFR, in particular to domain III of the EGFR. The specific binding to the EGFR preferably reduces or inhibits one or more biological activities of the EGFR in vivo. In particular, it preferably blocks the binding of a ligand to the EGFR, in particular the binding of EGF and/or TGFα, and/or dimerization of the EGFR.

Furthermore, the humanized antibody may exhibit antigen binding properties similar to those of a reference antibody comprising a heavy chain variable region with the amino acid sequence of SEQ ID NO: 4 and a light chain variable region with the amino acid sequence of SEQ ID NO: 8. Preferably, the reference antibody is the human/mouse chimeric antibody Cetuximab. In particular, the humanized antibody according to the invention may specifically bind to the same antigen, preferably the same epitope, as the reference antibody, and may preferably bind to said antigen or epitope, respectively, with a comparable affinity. That is, the humanized antibody preferably binds to the antigen or epitope with an affinity having a dissociation constant which is at most 1000-fold higher than that of the reference antibody, more preferably at most 200-fold higher, at most 100-fold higher, at most 20-fold higher or at most 10-fold higher. Most preferably, the dissociation constant is about the same as that of the reference antibody, in particular being no more than 2-fold higher. Moreover, the humanized antibody preferably shows cross-specificity with the reference antibody comprising a heavy chain variable region with the amino acid sequence of SEQ ID NO: 4 and a light chain variable region with the amino acid sequence of SEQ ID NO: 8. In particular, the humanized antibody is able to block the binding of the reference antibody to EGFR if present in a high enough concentration. This may be possible if the binding of the reference antibody to EGFR is hindered when the humanized antibody according to the invention is already bound to the antigen EGFR. The inhibition of the binding of the reference antibody may be due to, for example, a steric hindrance, i.e. the humanized antibody according to the invention occupies a part of the space which the reference antibody would need in order to properly bind to EGFR, or a conformational hindrance, i.e. due to the binding of the humanized antibody according to the invention the epitope of the reference antibody adopts a conformation which is unfavorable for the binding of the reference antibody.

In one embodiment, at least 2 and preferably all of the framework regions 1, 2 and 3 of the heavy chain variable region of the humanized antibody according to the invention are derived from or correspond to the human germline VH gene 4-59*01 coding for an amino acid sequence comprising SEQ ID NO: 31. Furthermore, the framework region 4 of the heavy chain variable region is preferably derived from or corresponds to the human germline gene JH1 coding for an amino acid sequence comprising SEQ ID NO: 32.

In one embodiment, at least one of framework regions 1, 2 and 3 of the light chain variable region of the humanized antibody according to the invention is derived from or corresponds to the human germline VL gene 6-21*01 coding for an amino acid sequence comprising SEQ ID NO: 33. Preferably, at least 2, more preferably all 3 of framework regions 1, 2 and 3 of the light chain variable region are derived from or correspond to the human germline VL gene 6-21*01 coding for an amino acid sequence comprising SEQ ID NO: 33. Furthermore, the framework region 4 of the light chain variable region is preferably derived from or corresponds to the human germline gene JK2 coding for an amino acid sequence comprising SEQ ID NO: 34.

In certain embodiments, the framework regions of the heavy chain variable region and/or the framework regions of the light chain variable region of the humanized antibody according to the invention comprise one or more amino acid substitution wherein the amino acid residue of the human-derived framework region preferably is replaced by the corresponding amino acid residue of the heavy chain variable region having the sequence of SEQ ID NO: 4 or of the light chain variable region having the sequence of SEQ ID NO: 8, respectively. A corresponding amino acid residue in this respect preferably is the amino acid residue at the same position according to the Kabat numbering as the amino acid residue which is substituted. Preferably, the framework regions of the heavy chain variable region of the humanized antibody according to the invention comprise no more than 30 of such amino acid substitutions, more preferably no more than 25, no more than 20, no more than 15, no more than 10 or no more than 6 of such amino acid substitutions. Furthermore, the framework regions of the light chain variable region of the humanized antibody according to the invention comprise no more than 20 of such amino acid substitutions, more preferably no more than 15, no more than 10, no more than 6, no more than 4 or no more than 2 of such amino acid substitutions.

In preferred embodiments, the heavy chain variable region of the humanized antibody according to the invention comprises at least one, preferably at least two or at least three, most preferably all four framework regions selected from the group consisting of (i) framework region 1 of the heavy chain variable region having the following amino acid sequences, the amino acid position corresponding to the numeration according to Kabat:

| FRH1 (SEQ ID NO: 9) | |
| --- | --- |
| Pos. | Amino acid |
| 1 | Q |
| 2 | V |
| 3 | Q |
| 4 | L |
| 5 | Q |
| 6 | E or Q |
| 7 | S |
| 8 | G |
| 9 | P |
| 10 | G |
| 11 | L |
| 12 | V |
| 13 | K |
| 14 | P |
| 15 | S |
| 16 | E |
| 17 | T |
| 18 | L |
| 19 | S |
| 20 | L |
| 21 | T |
| 22 | C |
| 23 | T |
| 24 | V |
| 25 | S |
| 26 | G |
| 27 | G or F |
| 28 | S |
| 29 | I |
| 30 | S |

(ii) framework region 2 of the heavy chain variable region having the following amino acid sequences, the amino acid position corresponding to the numeration according to Kabat:

| FRH2 (SEQ ID NO: 10) | |
| --- | --- |
| Pos. | Amino acid |
| 36 | W |
| 37 | I |
| 38 | R |
| 39 | Q |
| 40 | P or S |
| 41 | P |
| 42 | G |
| 43 | K |
| 44 | G |
| 45 | L |
| 46 | E |
| 47 | W |
| 48 | I |
| 49 | G |

(iii) framework region 3 of the heavy chain variable region having the following amino acid sequences, the amino acid position corresponding to the numeration according to Kabat:

| FRH3 (SEQ ID NO: 11) | |
|---|---|
| Pos. | Amino acid |
| 66 | R |
| 67 | V |
| 68 | T |
| 69 | I |
| 70 | S or N |
| 71 | V or K |
| 72 | D |
| 73 | T or N |
| 74 | S |
| 75 | K |
| 76 | N or S |
| 77 | Q |
| 78 | F or V |
| 79 | S |
| 80 | L or F |
| 81 | K |
| 82 | L or M |
| 82a | S |
| 82b | S |
| 82c | V |
| 83 | T |
| 84 | A |
| 85 | A or N |
| 86 | D |
| 87 | T |
| 88 | A |
| 89 | V |
| 90 | Y |
| 91 | Y |
| 92 | C |
| 93 | A |
| 94 | R |

(iv) framework region 4 of the heavy chain variable region having the following amino acid sequences, the amino acid position corresponding to the numeration according to Kabat:

| FRH4 (SEQ ID NO: 12) | |
|---|---|
| Pos. | Amino acid |
| 103 | W |
| 104 | G |
| 105 | Q |
| 106 | G |
| 107 | T |
| 108 | L |
| 109 | V |
| 110 | T |
| 111 | V |
| 112 | S |
| 113 | A |

In further preferred embodiments, the light chain variable region of the humanized antibody according to the invention comprises at least one, preferably at least two or at least three, most preferably all four framework regions selected from the group consisting of (v) framework region 1 of the light chain variable region having the following amino acid sequences, the amino acid position corresponding to the numeration according to Kabat:

| FRL1 (SEQ ID NO: 13) | |
|---|---|
| Pos. | Amino acid |
| 1 | E |
| 2 | I |
| 3 | V |
| 4 | L |
| 5 | T |
| 6 | Q |
| 7 | S |
| 8 | P |
| 9 | D |
| 10 | F |
| 11 | Q or L |
| 12 | S |
| 13 | V |
| 14 | T |
| 15 | P |
| 16 | K |
| 17 | E |
| 18 | K |
| 19 | V |
| 20 | T |
| 21 | I or F |
| 22 | T |
| 23 | C |

(vi) framework region 2 of the light chain variable region having the following amino acid sequences, the amino acid position corresponding to the numeration according to Kabat:

| FRL2 (SEQ ID NO: 14) | |
|---|---|
| Pos. | Amino acid |
| 35 | W |
| 36 | Y |
| 37 | Q |
| 38 | Q |
| 39 | K |
| 40 | P |
| 41 | D |
| 42 | Q |
| 43 | S |
| 44 | P |
| 45 | K or R |
| 46 | L |
| 47 | L |
| 48 | I |
| 49 | K |

(vii) framework region 3 of the light chain variable region having the following amino acid sequences, the amino acid position corresponding to the numeration according to Kabat:

| FRL3 (SEQ ID NO: 15) | |
|---|---|
| Pos. | Amino acid |
| 57 | G |
| 58 | V |
| 59 | P |
| 60 | S |
| 61 | R |
| 62 | F |
| 63 | S |
| 64 | G |
| 65 | S |

-continued

| FRL3 (SEQ ID NO: 15) | |
|---|---|
| Pos. | Amino acid |
| 66 | G |
| 67 | S |
| 68 | G |
| 69 | T |
| 70 | D |
| 71 | F |
| 72 | T |
| 73 | L |
| 74 | T |
| 75 | I |
| 76 | N |
| 77 | S |
| 78 | L |
| 79 | E |
| 80 | A |
| 81 | E |
| 82 | D |
| 83 | A or I |
| 84 | A |
| 85 | T or D |
| 86 | Y |
| 87 | Y |
| 88 | C |

(viii) framework region 4 of the light chain variable region having the following amino acid sequences, the amino acid position corresponding to the numeration according to Kabat:

| FRL4 (SEQ ID NO: 16) | |
|---|---|
| Pos. | Amino acid |
| 98 | F |
| 99 | G |
| 100 | Q or A |
| 101 | G |
| 102 | T |
| 103 | K |
| 104 | L |
| 105 | E |
| 106 | I |
| 107 | K |
| 108 | R |

Preferably, the humanized antibody according to the invention comprises a heavy chain variable region comprising the amino acid sequence of SEQ ID NO: 17 and/or a light chain variable region comprising the amino acid sequence of SEQ ID NO: 26. The heavy chain variable region preferably comprises an amino acid sequence selected from the group consisting of SEQ ID NOs: 18 to 25, in particular the amino acid sequence of SEQ ID NO: 20. Furthermore, the light chain variable region preferably comprises an amino acid sequence selected from the group consisting of SEQ ID NOs: 27 to 30, in particular the amino acid sequence of SEQ ID NO: 29. Particularly preferred is a humanized antibody comprising a heavy chain variable region comprising the amino acid sequence of SEQ ID NO: 20 and a light chain variable region comprising the amino acid sequence of SEQ ID NO: 29.

In one embodiment, the humanized antibody according to the invention has a glycosylation site in its heavy chain variable region. Preferably, the glycosylation site is at position 85 of the heavy chain variable region according to the Kabat numbering. In this embodiment, the humanized antibody preferably comprises an asparagine at position 85 of the heavy chain variable region according to the Kabat numbering, corresponding to amino acid residue 88 of SEQ ID NO: 17. The presence of this glycosylation site may result in the glycosylation of the heavy chain variable region of the humanized antibody. Thereby, important features of the antibody may be influenced and/or regulated such as the antigen binding affinity, the antigen specificity and/or the circulation half-life.

In another embodiment, the humanized antibody according to the invention does not have a glycosylation site in its heavy chain variable region. In this embodiment, the heavy chain variable region preferably does not comprise an asparagine at position 85 according to the Kabat numbering, corresponding to amino acid residue 88 of SEQ ID NO: 17. In particular, it comprises an alanine residue at this position. Alternatively or additionally, the heavy chain variable region preferably does not comprise a serine or threonine at position 87 according to the Kabat numbering, corresponding to amino acid residue 90 of SEQ ID NO: 17, and/or comprises a proline at position 86 according to the Kabat numbering, corresponding to amino acid residue 89 of SEQ ID NO: 17.

In particular preferred embodiments, the humanized antibody according to the invention does not have a glycosylation site in its heavy chain and light chain regions, preferably it does not have a glycosylation site in its Fab part. Preferably, a glycosylation site in the Fab part of a non-humanized anti-EGFR antibody is removed during humanization to obtain the humanized antibody according to the present invention. The glycosylation site in the reference antibody may be removed by any method known in the art and in particular by altering the amino acid sequence. Preferably, the glycosylation site is removed by adding, substituting and/or deleting one or more amino acids in the amino acid sequence of the antibody. In particular, the amino acid of the glycosylation site which functions as acceptor of the carbohydrate chain is deleted or substituted by another amino acid which cannot function as acceptor for the carbohydrate chain, and/or the recognition sequence of the enzyme responsible for glycosylation of the antibody, in particular oligosaccharyltransferase, is altered so that the enzyme cannot recognize the amino acid sequence and thus, cannot transfer the carbohydrate chain onto the polypeptide chain of the antibody. In particular, for removing a N-glycosylation site, the amino acid sequence of the glycosylation site Asn Xaa Ser/Thr, wherein Xaa is any amino acid residue preferably except Pro, is altered so that (i) the Asn is deleted or substitute for any other amino acid, (ii) the Ser or Thr is deleted or substituted with any amino acid except Ser and Thr, (iii) the Xaa is deleted or substituted with Pro, and/or (iv) a further amino acid is introduced between the Asn and the Ser/Thr.

By excluding any glycosylation at the heavy chain variable region an in particular in the Fab part of the humanized antibody, any possible negative influence of this glycosylation can be excluded. In particular, it was found that the circulation half-life is significantly enhanced in primates, in particular in humans, if no glycosylation site is present in the Fab part. This is an important advantage over chimeric versions of said antibody, which all comprise a glycosylation site at this position.

In preferred embodiments, the humanized antibody according to the invention is glycosylated. Preferably, the humanized antibody is glycosylated at the Fc region, in particular at the CH2 domain if the humanized antibody is an IgG-type antibody. Additionally, the humanized antibody may be glycosylated at the Fab region, preferably in the heavy chain variable region, depending on the presence of a glycosylation site in the heavy chain variable region. However, preferably the humanized antibody is only glycosylated at the Fc region. The glycosylation pattern of the humanized antibody according to the invention preferably is a human glycosylation pattern, that is, a glycosylation pattern also found on naturally occurring antibodies produced by the human body. Furthermore, the glycosylation pattern preferably modulates, in particular enhances one or more properties or activities of the antibody. In particular, it preferably enhances the antibody's binding affinity to its specific epitope or its antigen specificity. Furthermore, the glycosylation pattern may modulate, in particular enhance the antibody's binding affinity to one or more of its downstream receptors such as Fc receptors, in particular Fc gamma, Fc alpha or Fc epsilon receptors. Additionally or alternatively, the glycosylation pattern may enhance its complement dependent cytotoxicity (CDC), and/or its antibody-dependent cell-mediated cytotoxicity (ADCC).

In certain embodiments, the antibody according to the invention preferably has a low amount of fucose and a low amount of sialic acid in the carbohydrates attached to one or more glycosylation sites in the Fc part of the antibody. In particular, in a composition comprising the antibodies or fragments or derivatives thereof of the present invention, preferably less than 30%, more preferably less than 20%, less than 15%, or less than 10% of the carbohydrates attached to the Fc part of the antibodies or fragments or derivatives thereof in the composition comprise a fucose unit. Likewise, in a composition comprising the antibodies or fragments or derivatives thereof of the present invention, preferably less than 30%, more preferably less than 20%, less than 15%, or less than 10% of the carbohydrates attached to the Fc part of the antibodies or fragments or derivatives thereof in the composition comprise a sialic acid unit. Low fucose content as well as low sialic acid content in the carbohydrates attached to the Fc part of the antibody enhances its ADCC activity. Furthermore, the antibody or fragment or derivative thereof preferably does not carry carbohydrate chains comprising the carbohydrate structure Galα(1→3)Galβ and/or N-glycolylneuraminic acid (NeuGc) residues. Moreover, in a composition comprising the antibodies or fragments or derivatives thereof of the present invention, preferably at least 25%, more preferably at least 40% of the sialic acid residues in the carbohydrate chains attached to the antibodies or fragments or derivatives thereof are coupled by a 2,6-linkage. The presence of Galα(1→3)Galβ structures or NeuGc as well as a high amount of 2,3-linked sialic acids may cause adverse immune reactions by the patient to which the antibody is administered.

To this end, the glycosylation pattern of the antibody or fragment or derivative thereof may be engineered or optimized, for example by using specific cell lines which are capable of producing the desired glycosylation pattern. Particularly preferred glycosylation patterns are those which are obtainable by expressing the humanized antibody in a cell line selected from the group consisting of K562, KG1, MUTZ-3, NM-F9, NM-D4, NM-H9D8, NM-H9D8-E6, NM H9D8-E6Q12, and GT-2x. These cell lines and their properties are described in detail in the PCT-application WO 2008/028686 A2.

The above described embodiments, features and properties regarding the humanized antibody according to the invention and its antigen and/or epitope binding properties can in the same manner be applied to the fragment or derivative thereof according to the invention, where appropriate.

Preferably, the fragment or derivative of the antibody according to the invention is selected from the group consisting of a Fab fragment, a F(ab)$_2$ fragment, a Fd fragment, a Fv fragment, a scFv fragment, a (Fv)$_2$ fragment, and a multibody. The antibody or fragment or derivative thereof may be a single chain construct comprising only one amino acid molecule, or a multi chain construct comprising more than one amino acid molecule which preferably are covalently connected to each other, for example by disulfide bonds.

The humanized antibody or fragment or derivative thereof according to the invention preferably is useful in medicine, in particular in therapy, diagnosis, prognosis and/or monitoring of a disease, in particular a disease as described herein, preferably cancer.

In a further aspect, the present invention provides a nucleic acid encoding the humanized antibody or fragment or derivative thereof according to the invention. The nucleic acid sequence of the nucleic acid according to the invention may have any nucleotide sequence suitable for encoding the antibody or fragment or derivative thereof according to the invention. However, preferably the nucleic acid sequence is at least partially adapted to the specific codon usage of the host cell or organism in which the nucleic acid according to the invention is to be expressed, in particular the human codon usage. The nucleic acid according to the invention may be double-stranded or single-stranded DNA or RNA, preferably double-stranded DNA such as cDNA or single-stranded RNA such as mRNA. It may be one consecutive nucleic acid molecule or it may be composed of several nucleic acid molecules, each coding for a different part of the antibody or fragment or derivative thereof according to the invention.

If the humanized antibody or fragment or derivative thereof according to the invention is a single chain construct, the nucleic acid according to the invention preferably is a single nucleic acid molecule containing a coding region which codes for the entire antibody or fragment or derivative thereof. If the humanized antibody or fragment or derivative thereof according to the invention is composed of more than one amino acid chain, the nucleic acid according to the invention may, for example, be a single nucleic acid molecule containing several coding regions each coding for one of the amino acid chains of the antibody or fragment or derivative thereof, preferably separated by regulatory elements such as IRES elements in order to generate separate amino acid chains, or the nucleic acid according to the invention may be composed of several nucleic acid molecules wherein each nucleic acid molecule comprises one or more coding regions each coding for one of the amino acid chains of the antibody or fragment or derivative thereof. In addition to the coding regions encoding the humanized antibody or fragment or derivative thereof according to the invention, the nucleic acid according to the invention may also comprise further nucleic acid sequences or other modifications which, for example, may code for other proteins, may influence the transcription and/or translation of the coding region(s), may influence the stability or other physical or chemical properties of the nucleic acid, or may have no function at all.

In a further aspect, the present invention provides an expression cassette or vector comprising a nucleic acid according to the invention and a promoter operatively connected with said nucleic acid. In addition, the expression cassette or vector may comprise further elements, in particular elements which are capable of influencing and/or regulating the transcription and/or translation of the nucleic acid according to the invention, the amplification and/or reproduction of the expression cassette or vector, the integration of the expression cassette or vector into the genome of a host cell, and/or the copy number of the expression cassette or vector in a host cell. Suitable expression cassettes and vectors comprising respective expression cassettes for expressing antibodies are well known in the prior art and thus, need no further description here.

Furthermore, the present invention provides a host cell comprising the nucleic acid according to the invention or the expression cassette or vector according to the invention. The host cell according to the invention may be any host cell. It may be an isolated cell or a cell comprised in a tissue. Preferably, the host cell is a cultured cell, in particular a primary cell or a cell of an established cell line, preferably a tumor-derived cell. Preferably, it is a bacterial cell such as *E. coli*, a yeast cell such as a *Saccharomyces* cell, in particular *S. cerevisiae*, an insect cell such as a Sf9 cell, or a mammalian cell, in particular a human cell such as a tumor-derived human cell, a hamster cell such as CHO, or a primate cell. In a preferred embodiment of the invention the host cell is derived from human myeloid leukaemia cells. Preferably, it is selected from the following cells or cell lines: K562, KG1, MUTZ-3, NM-F9, NM-D4 or a cell or cell line derived therefrom, or a mixture of cells or cell lines comprising at least one of those aforementioned cells. The host cell is preferably selected from the group consisting of NM-F9, NM-D4, NM-H9D8, NM-H9D8-E6, NM H9D8-E6Q12, GT-2x and a cell or cell line derived from anyone of said host cells, or a mixture of cells or cell lines comprising at least one of those aforementioned cells. These cell lines and their properties are described in detail in the PCT-application WO 2008/028686 A2. In preferred embodiments, the host cell is optimized for expression of glycoproteins, in particular antibodies, having a specific glycosylation pattern. Preferably, the codon usage in the coding region of the nucleic acid according to the invention and/or the promoter and the further elements of the expression cassette or vector are compatible with and, more preferably, optimized for the type of host cell used. Preferably, the humanized antibody or fragment or derivative thereof according to the invention is produced by a host cell or cell line as described above.

In a further aspect, the present invention provides a conjugate comprising the antibody or fragment or derivate thereof according to the invention conjugated to a further agent such as a detectable marker or a therapeutically active substance. The further agent preferably is useful in therapy, diagnosis, prognosis and/or monitoring of a disease, in particular cancer. For example, the further agent may be selected from the group consisting of antibodies or fragments of antibodies, in particular those of different species and/or different specificity, enzymes, interaction domains, stabilizing domains, signaling sequences, detectable labels, fluorescent dyes, toxins, catalytic antibodies, cytolytic components, immunomodulators, immunoeffectors, MHC class I or class II antigens, chelators for radioactive labeling, radioisotopes, liposomes, transmembrane domains, viruses, and cells. It may be covalently, in particular by fusion or chemical coupling, or non-covalently attached to the antibody or fragment or derivative thereof. A particular preferred further agent is a radionuclide or a cytotoxic agent capable of killing cancer cells, such as a chemotherapeutic agent, in particular alkylating agents such as cisplatin, anti-metabolites, plant alkaloids and terpenoids, vinca alkaloids, podophyllotoxin, taxanes such as taxol, topoisomerase inhibitors such as irinotecan and topotecan, or antineoplastics such as doxorubicin.

In another aspect, the present invention provides a composition comprising the humanized antibody or fragment or derivative thereof according to the invention, the nucleic acid according to the invention, the expression cassette or vector according to the invention, the host cell according to the invention, or the conjugate according to the invention. The composition may also contain more than one of these components. Furthermore, the composition may comprise one or more further components selected from the group consisting of solvents, diluents, and excipients Preferably, the composition is a pharmaceutical composition. In this embodiment, the components of the composition preferably are all pharmaceutically acceptable. The composition may be a solid or fluid composition, in particular a—preferably aqueous—solution, emulsion or suspension or a lyophilized powder.

In a further aspect, the invention provides the humanized antibody or fragment or derivative thereof according to the invention, the nucleic acid according to the invention, the expression cassette or vector according to the invention, the host cell according to the invention, the conjugate according to the invention, or the composition according to the invention for use in medicine. Preferably, the use in medicine is a use in the treatment, prognosis, diagnosis and/or monitoring of a disease such as, for example, diseases associated with abnormal cell growth such as cancer. In a preferred embodiment, the disease is cancer. Preferably the cancer is selected from the group consisting of colorectal cancer, head and neck cancer, and lung cancer as well as metastases originating therefrom. In particular, the cancer is EGFR-expressing metastatic colorectal cancer, squamous cell carcinoma of the head and neck, or non-small cell lung carcinoma.

For use in the treatment of diseases associated with abnormal cell growth such as cancer, the humanized antibody or fragment or derivative thereof according to the invention may be coupled to a further agent as described above, wherein the further agent preferably is a cytotoxic agent such as a radionuclide or a cytotoxin. Furthermore, the humanized antibody or fragment or derivative thereof may be engineered so as to enhance its ability to activate the patient's immune response, in particular the ability to activate ADCC (antibody-dependent cell-mediated cytotoxicity) and/or CDC (complement dependent cytotoxicity). For example, this may be achieved by optimizing the amino acid sequence and/or the glycosylation pattern of the antibody, in particular of its constant regions.

Furthermore, the treatment of diseases associated with abnormal cell growth such as cancer using the humanized antibody or fragment or derivative thereof according to the invention may be combined with the treatment using a further agent, in particular a chemotherapy. The further agent preferably is a cytotoxic agent or a radionuclide, in particular alkylating agents such as cisplatin, anti-metabolites, plant alkaloids and terpenoids, vinca alkaloids, podophyllotoxin, taxanes such as taxol, topoisomerase inhibitors such as irinotecan and topotecan, or antineoplastics such as doxorubicin.

For use as detection agent in diagnosis, prognosis and/or monitoring of a disease, the antibody or fragment or derivative thereof according to the invention preferably is coupled to a labeling agent which is capable of producing a detectable signal. In particular, said labeling agent may be a radionuclide, a fluorophore or an enzyme.

FIGURES

Figure 3:
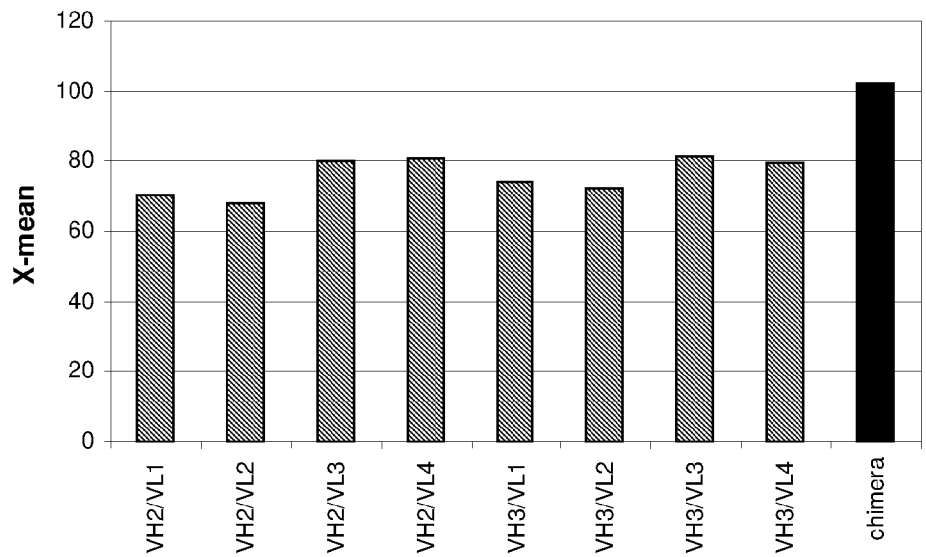
Figure 3:
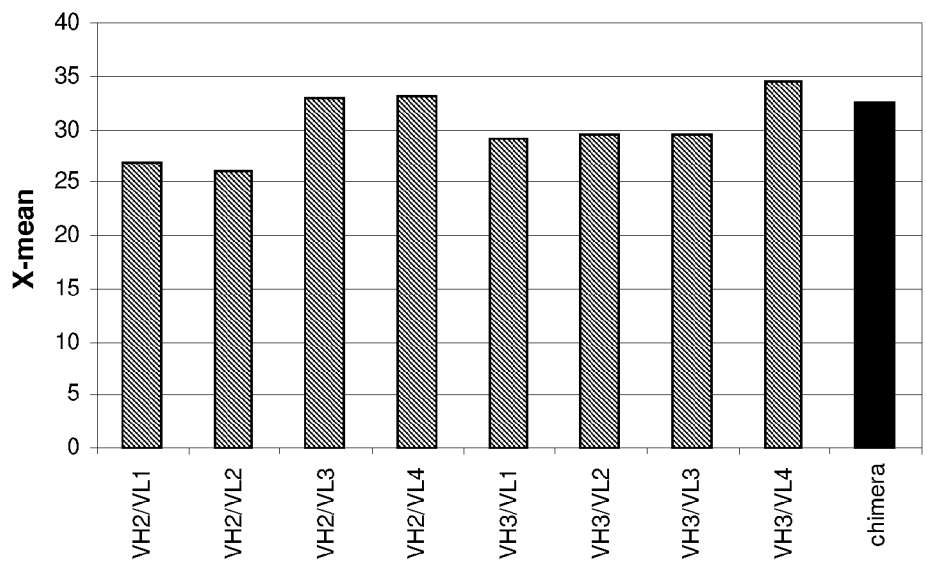

FIG. 3 shows the binding of several humanized anti-EGFR antibodies to HT-29 cells expressing EGFR in a FACS assay. Shown is the mean signal strength of the cells labeled with 100 ng/ml (A) or 10 ng/ml (B) of the respective antibody. As control, the chimeric mouse/human anti-EGFR antibody was used.

Figure 4:
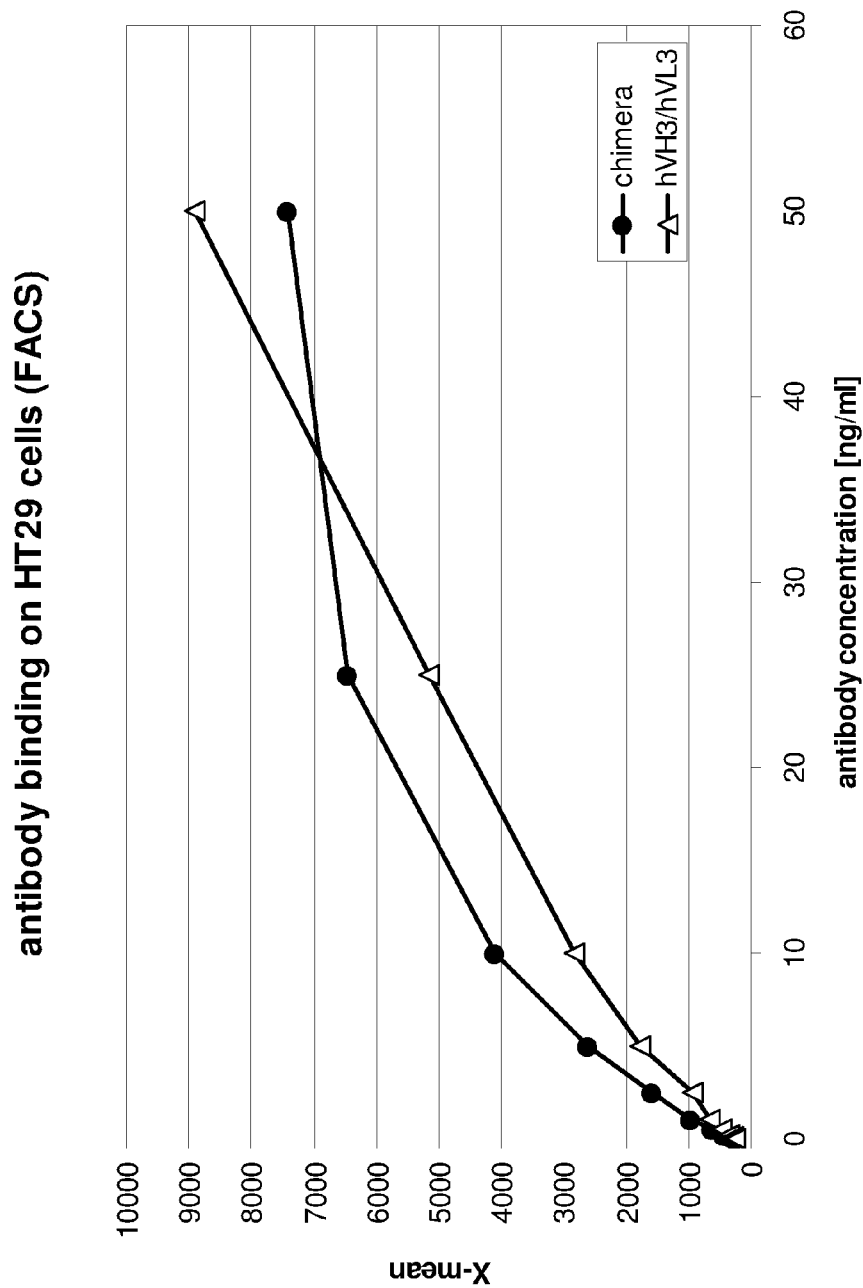

FIG. 4 shows the concentration dependency of the binding of humanized anti-EGFR antibody variant VH3/VL3 to HT-29 cells expressing EGFR in a FACS assay. As control, the chimeric mouse/human anti-EGFR antibody was used.

Figure 5:
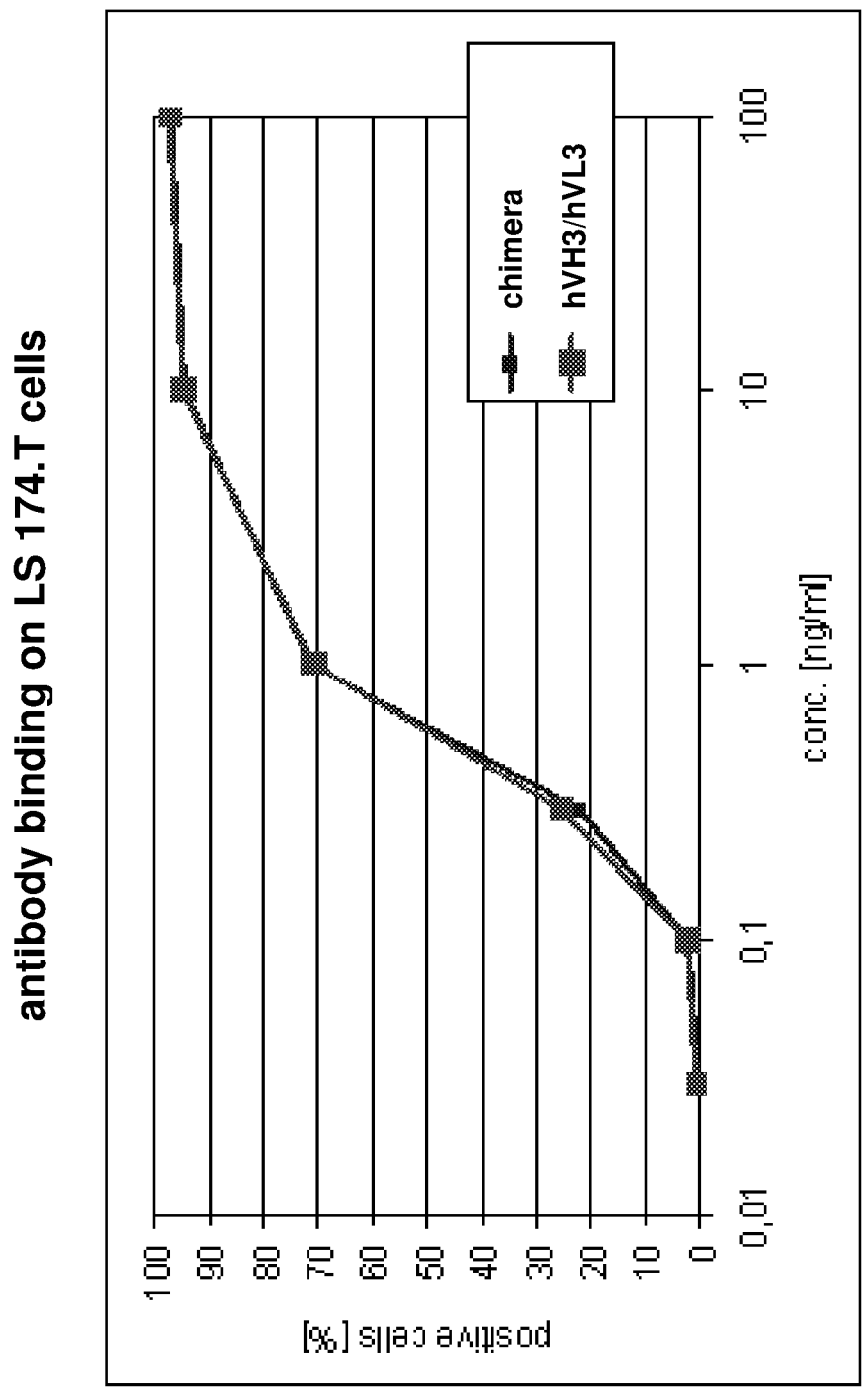

FIG. 5 shows the concentration dependency of the binding of humanized anti-EGFR antibody variant VH3/VL3 to LS 174.T cells expressing EGFR in a FACS assay. As control, the chimeric mouse/human anti-EGFR antibody was used.

Figure 6:
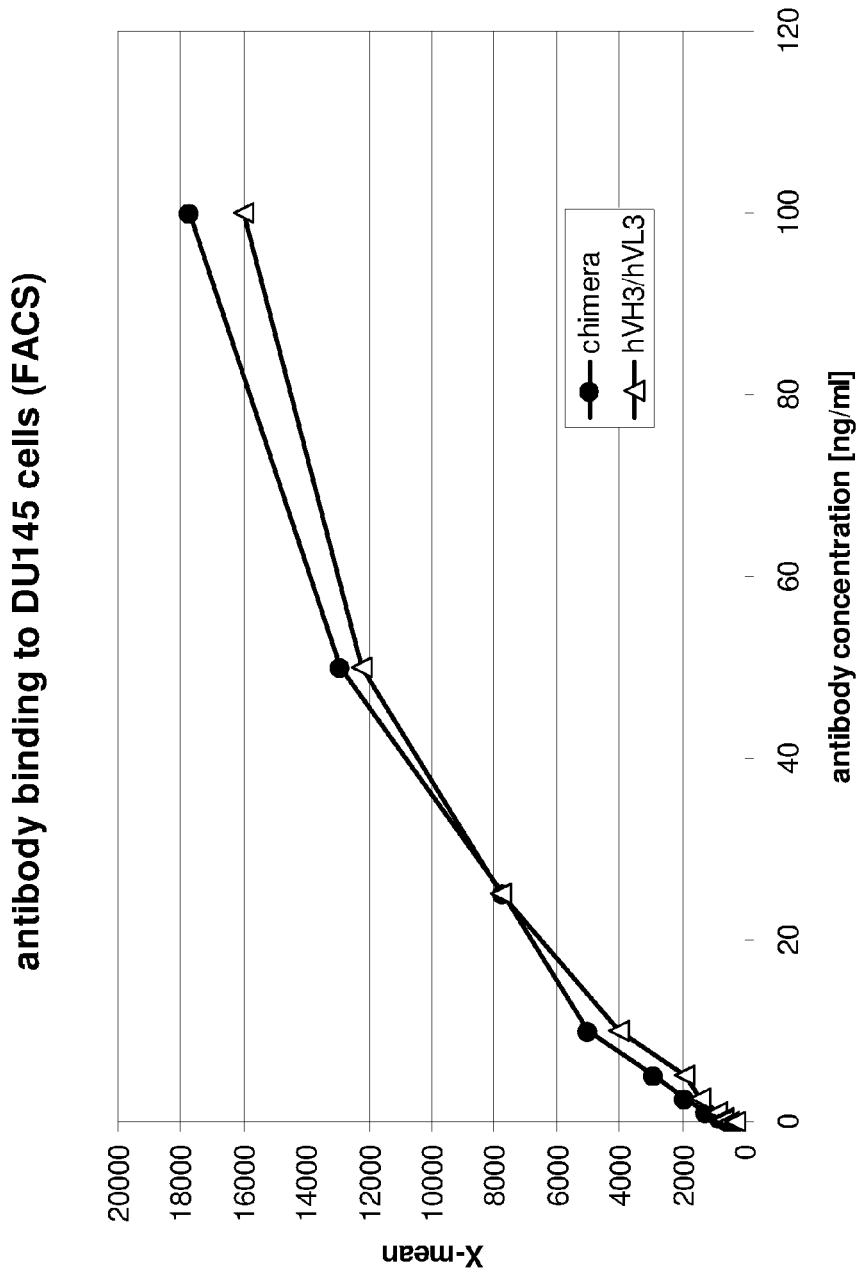

FIG. 6 shows the concentration dependency of the binding of humanized anti-EGFR antibody variant VH3/VL3 to DU145 cells expressing EGFR in a FACS assay. As control, the chimeric mouse/human anti-EGFR antibody was used.

Figure 7:
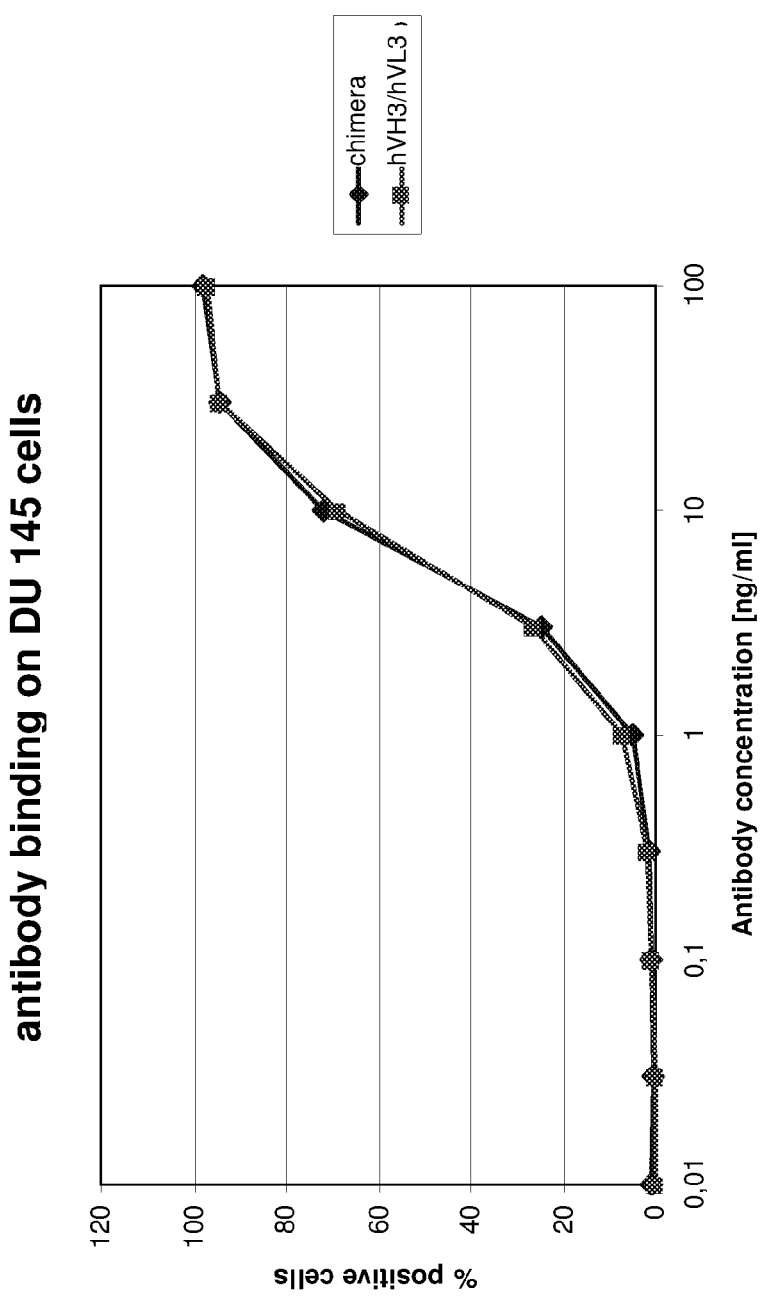

FIG. 7 shows the concentration dependency of the binding of humanized anti-EGFR antibody variant VH3/VL3 to DU145 cells expressing EGFR in a FACS assay. As control, the chimeric mouse/human anti-EGFR antibody was used.

Figure 8:
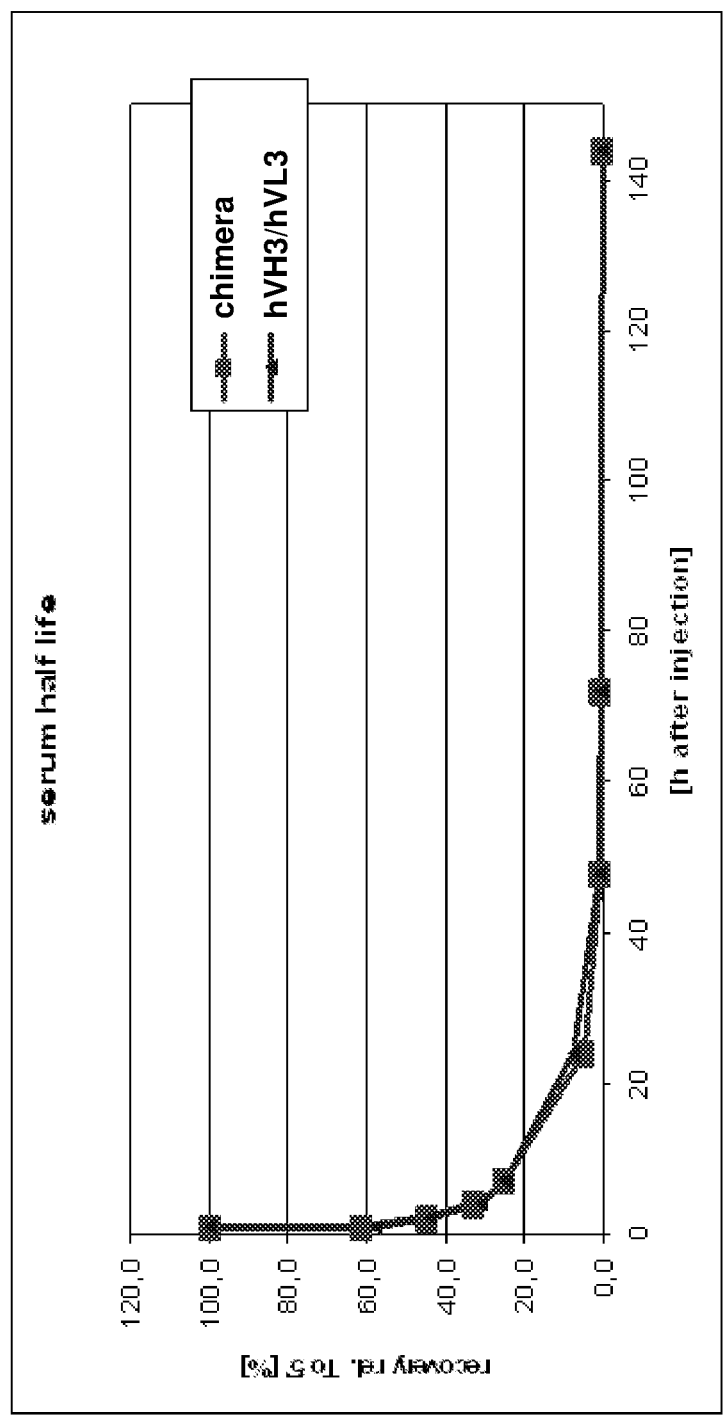

FIG. 8 shows the pharmacokinetics of humanized anti-EGFR antibody variant VH3/VL3 injected into mice. As control, the chimeric mouse/human anti-EGFR antibody was used.

Figure 9:
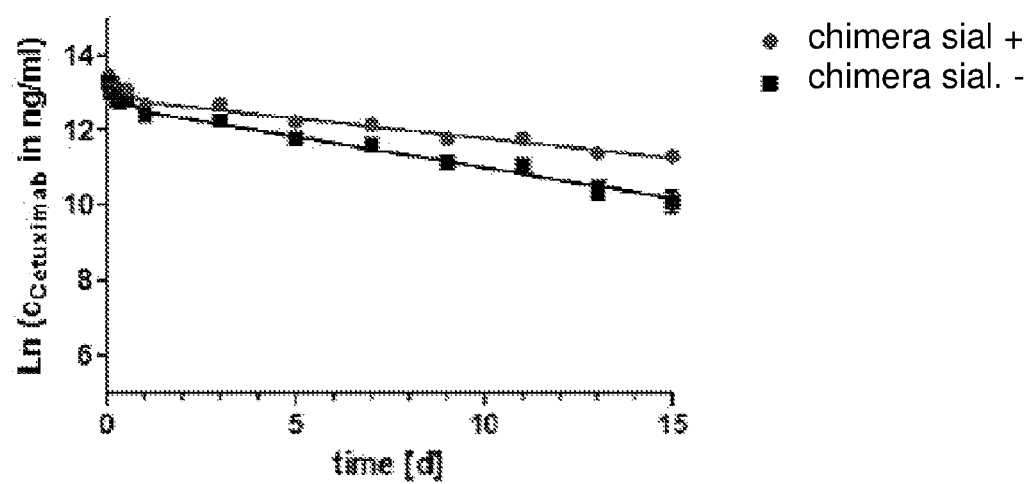

FIG. 9 shows the pharmacokinetics of chimeric Cetuximab either expressed in a human myeloid leukemia cell line having a high sialylation activity (chimera sial. +) or expressed in the mouse myeloid cell line SP2/0 having a low sialylation activity (chimera sial. −) in cynomolgus monkeys.

Figure 10:
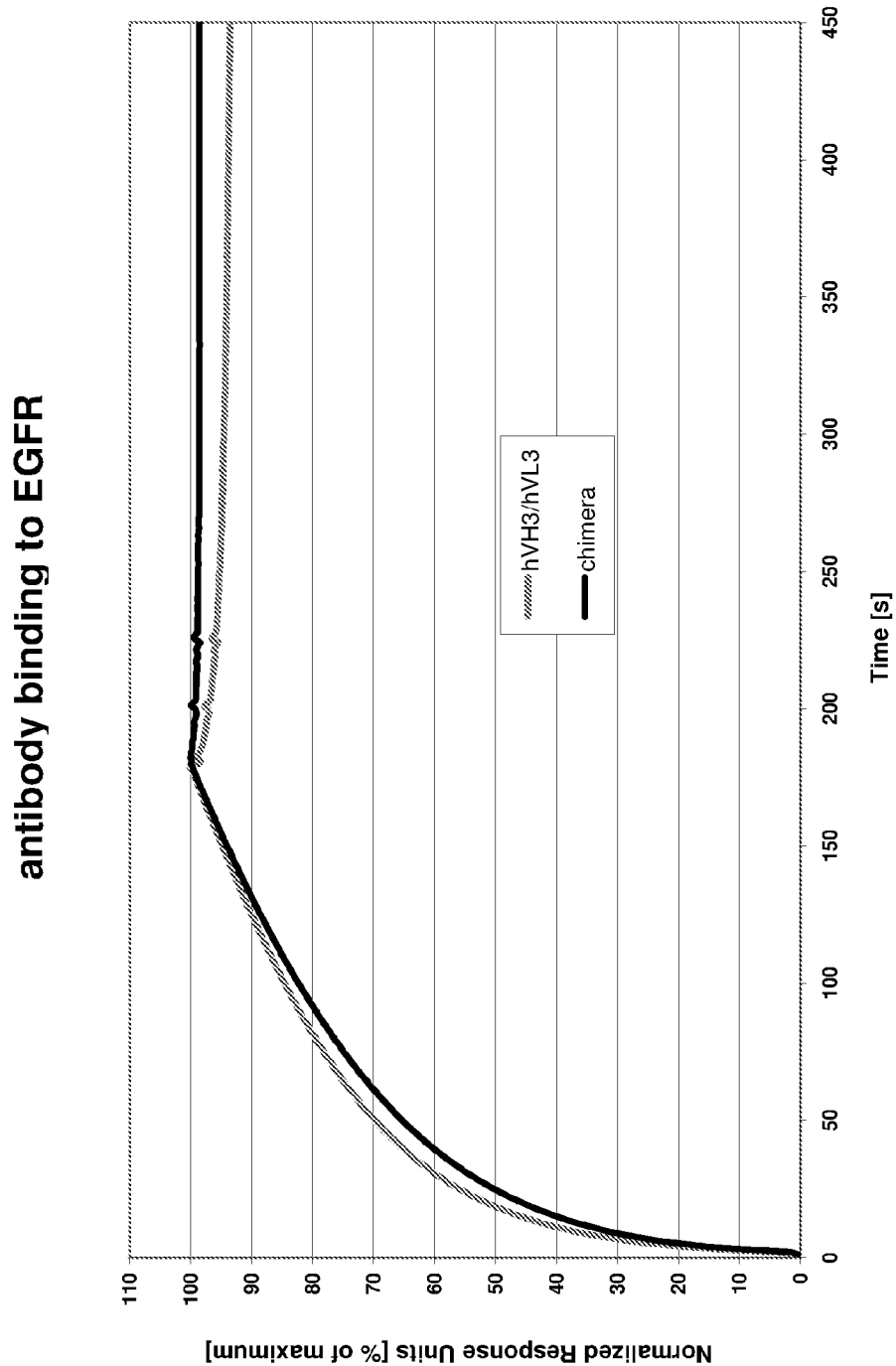

FIG. 10 shows a comparison of the binding of the chimeric mouse/human anti-EGFR antibody and the humanized anti-EGFR antibody variant VH3/VL3 to the EGF receptor by surface plasmon resonance (Biacore®), normalized to maximal binding. The used antibody concentration was 1.5 µg/30 µL.

Figure 11:
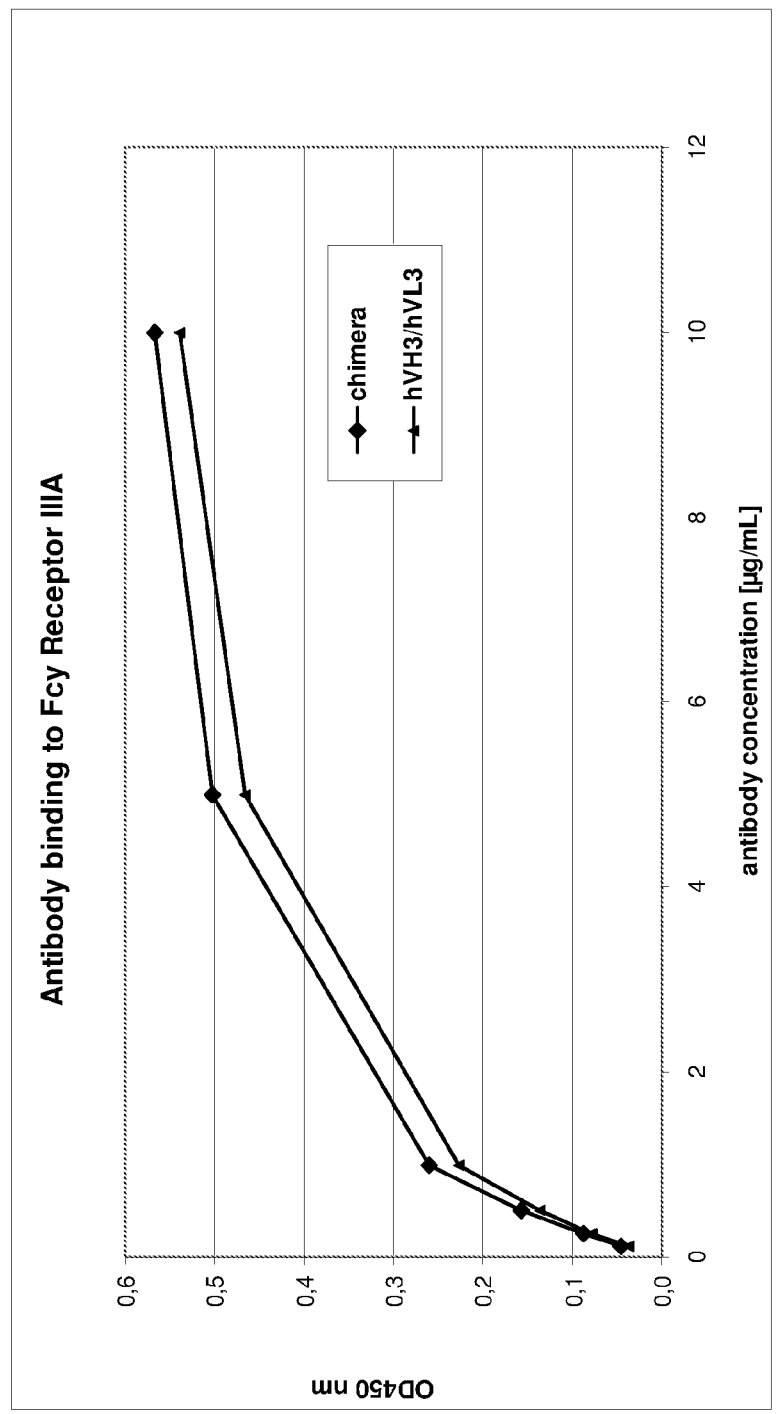

FIG. 11 shows a comparison of the binding of the chimeric mouse/human anti-EGFR antibody and the humanized anti-EGFR antibody variant VH3/VL3 to the Fc gamma Receptor IIIA.

Figure 12:
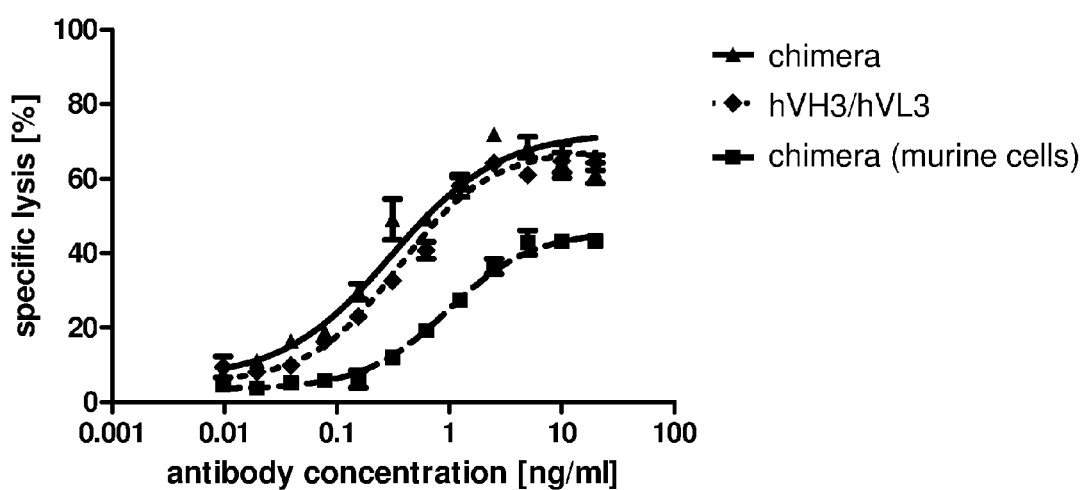

FIG. 12 shows the results of an ADCC assay with the humanized anti-EGFR antibody variant VH3/VL3 expressed in human cells and the chimeric mouse/human anti-EGFR antibody expressed in human or murine cells on A549 cells. Incubation time was 5 h, E:T ratio 80:1. Results are given as mean values of triplicates±SEM.

Figure 13:
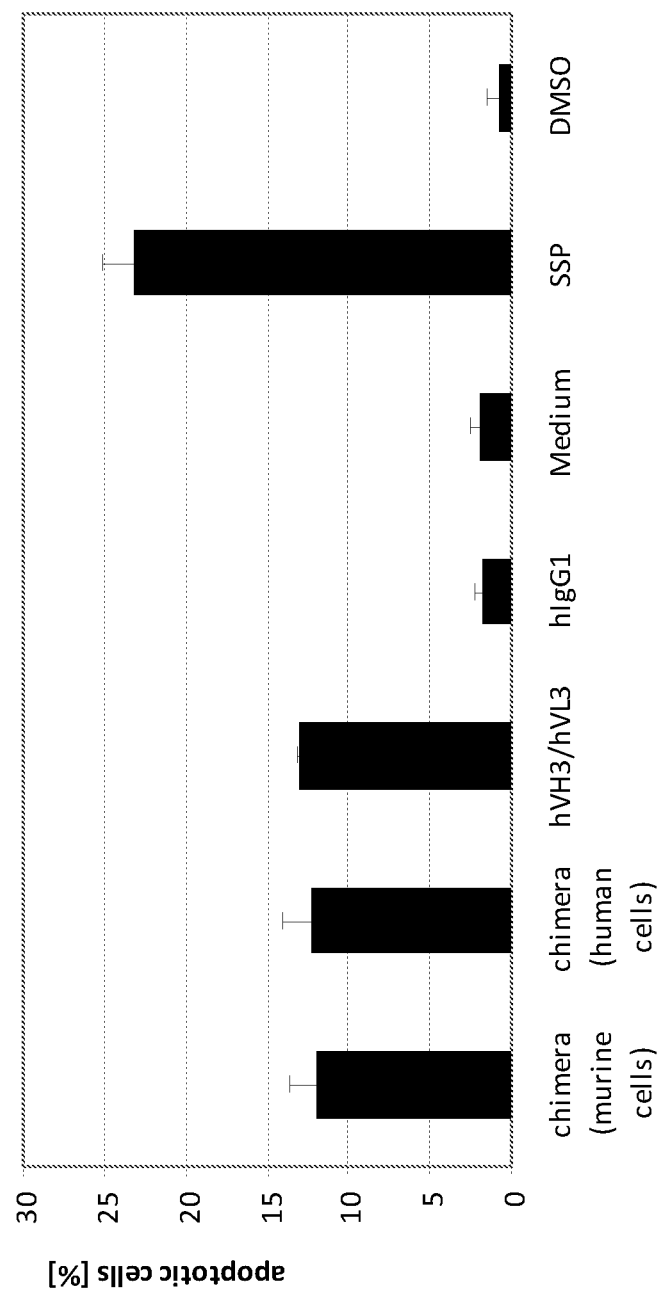

FIG. 13 shows the results of an apoptosis with the humanized anti-EGFR antibody variant VH3/VL3 expressed in human cells and the chimeric mouse/human anti-EGFR antibody expressed in human or murine cells on A431 cells. Incubation time was 24 h, antibody concentration was 1 µg/ml. Apoptotic cells were calculated as percentage of active Caspase-3 positive cells minus isotype control. Results are given as mean values of duplicates±SD.

Figure 14:
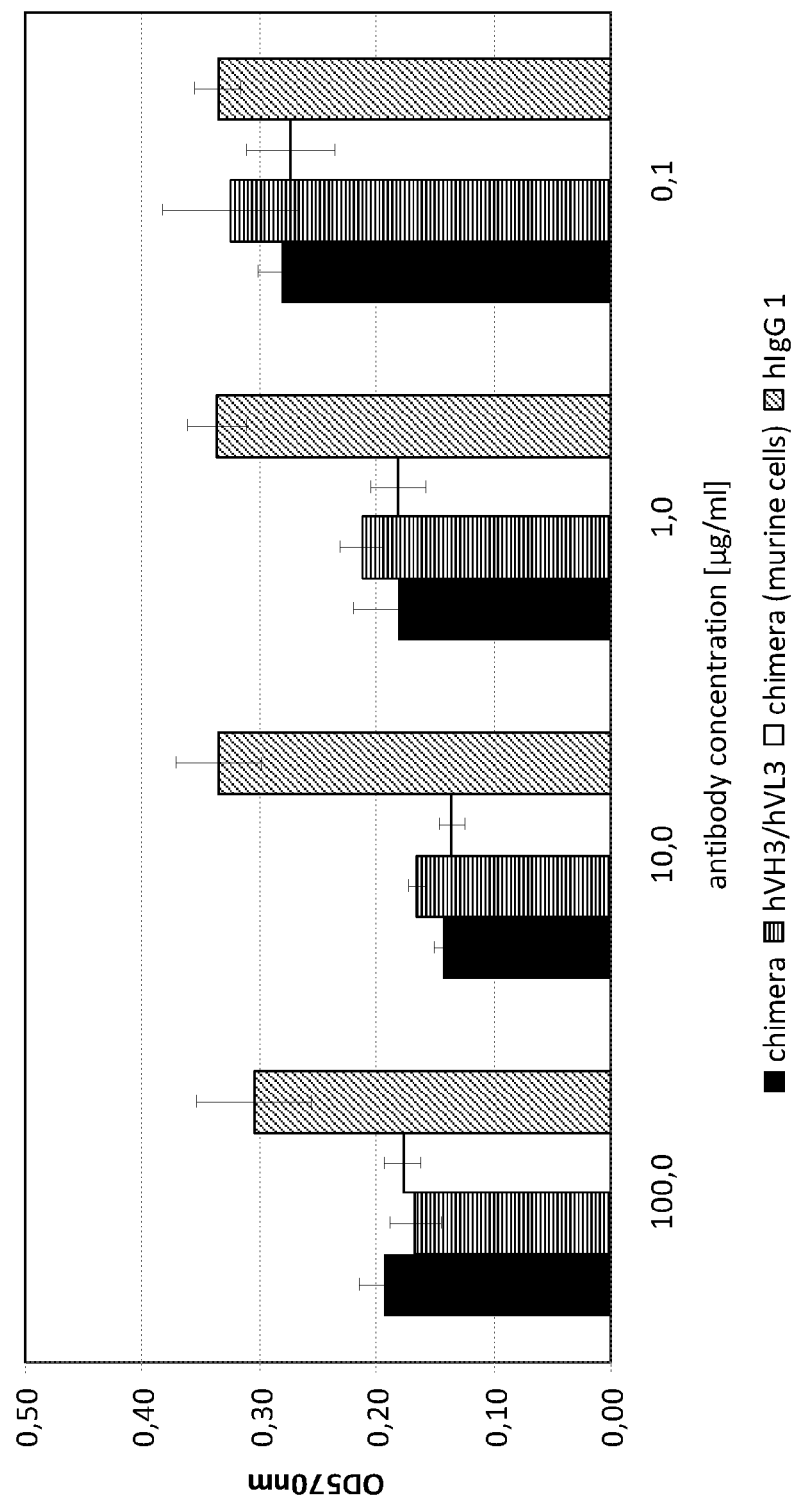

FIG. 14 shows the results of an MTT proliferation assay with the humanized anti-EGFR antibody variant VH3/VL3 expressed in human cells and the chimeric mouse/human anti-EGFR antibody expressed in human or murine cells on A431 cells. Incubation time was 4 days, results are given as mean values of quadruplets±SD.

EXAMPLES

Example 1

Humanization of the Murine Heavy and Light Chain Variable Regions of an Anti-EGFR Antibody The nucleic acid sequences coding for the heavy and light chain variable regions (VH, SEQ ID NO: 4, and VL, SEQ ID NO: 8) of a monoclonal antibody directed against an epitope in the extracellular ligand binding domain of human EGFR1 were ligated to the genomic sequences of the human constant γ1 region (CH) and the human constant κ region (CL), respectively.

On the basis of these chimeric clones, humanized antibodies were constructed. To this end, point mutations were introduced into the nucleic acid sequences of the murine framework regions of VH and VL in order to generate the corresponding human framework regions. The target human framework regions were selected from a human germ line antibody library. In particular, the most related framework regions were chosen from the library depending on their overall sequence similarity and their CDR loop classification. All data obtained were considered to design a set of different variable sequences of humanized variable light (4 variants) and variable heavy chains (8 variants). Some of the variants contain back-mutations to the murine sequence on critical positions. The humanized variants of the light chain variable region were cloned in a κ-chain vector and the humanized variants of the heavy chain variable region were cloned in a γ-chain vector.

By the above described method, the following humanized antibody heavy and light chains variable regions were obtained.

TABLE 1

| heavy chain variable region | SEQ ID | light chain variable region | SEQ ID |
|---|---|---|---|
| mVH | 4 | mVL | 8 |
| VH1 | 18 | VL1 | 27 |
| VH2 | 19 | VL2 | 28 |
| VH3 | 20 | VL3 | 29 |
| VH4 | 21 | VL4 | 30 |
| VH5 | 22 | | |
| VH6 | 23 | | |
| VH7 | 24 | | |
| VH8 | 25 | | | mVH and mVL represent the murine heavy and light chain variable regions, respectively, which were used as basis for the humanization.

Example 2

Binding of the Humanized Antibody Variants to Immobilized EGFR

Figure 1:
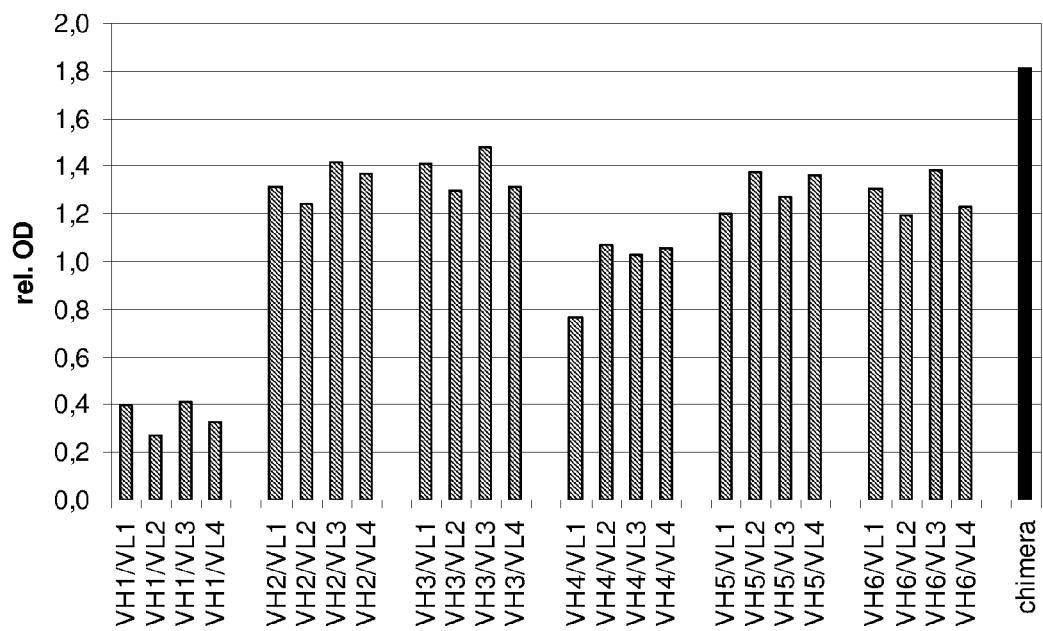
FIG. 1 shows the binding of several humanized anti-EGFR antibodies to their antigen in an ELISA assay. As control, the chimeric mouse/human anti-EGFR antibody was used.
Figure 2:
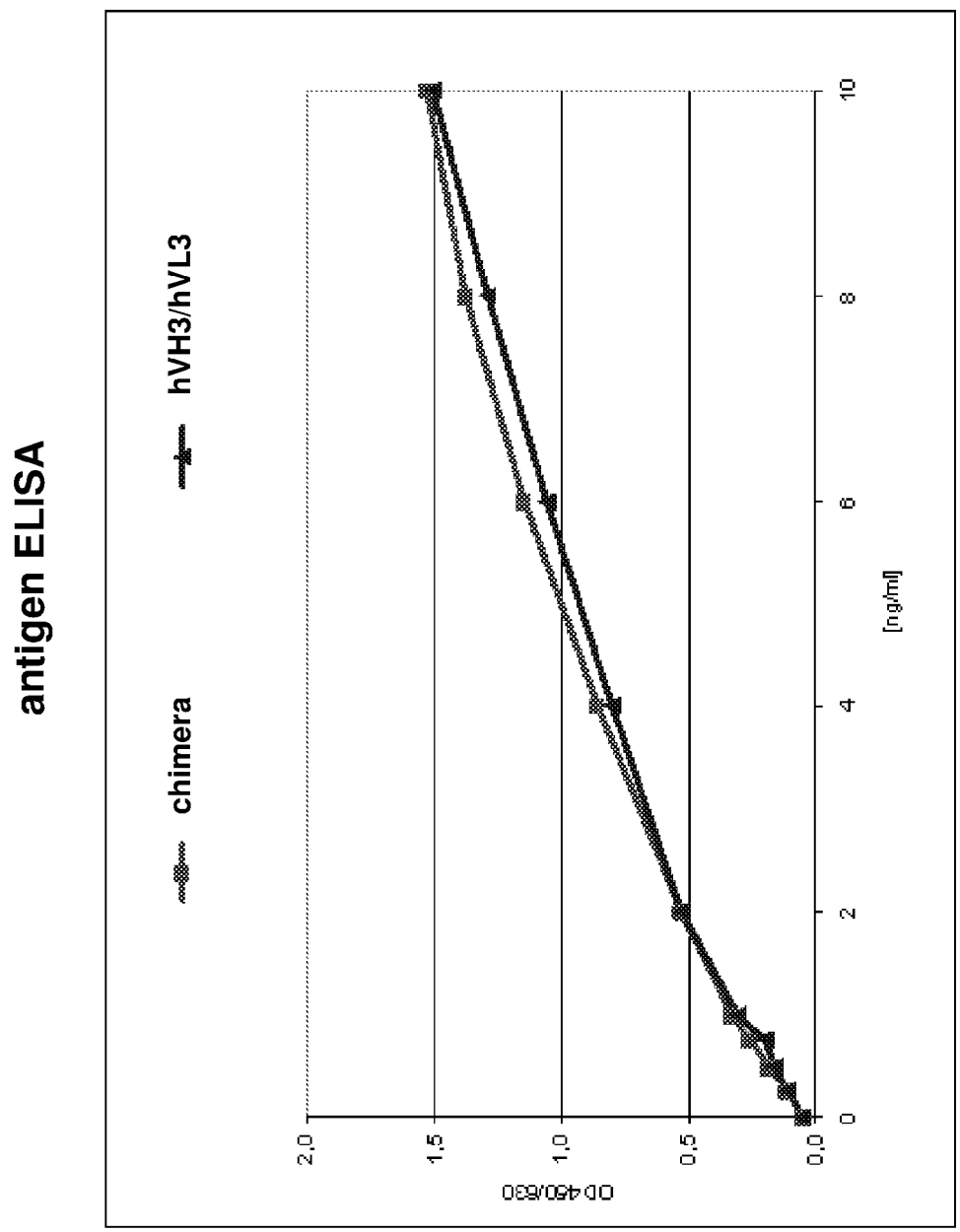
FIG. 2 shows an antigen ELISA binding study of humanized anti-EGFR antibody variant VH3/VL3 in comparison to the chimeric mouse/human anti-EGFR antibody.

Following expression of the different constructs in COS cells, the titer of the humanized antibody variants was determined and their concentration adjusted. Then, the humanized antibodies were screened in an antigen ELISA. Exemplary results of one screening round are shown in FIG. 1. All variants showed a significant binding to the antigen. Good antigen binding was observed for humanized antibody variants comprising a heavy chain variable region selected from VH2, VH3, VH5 and VH6. In particular the variant VH3/VL3 showed good results. Furthermore, also antibodies comprising the heavy chain variable region VH7 or VH8 showed good antigen binding. A direct comparison in antigen ELISA of the chimeric antibody and the humanized antibody variant hVH3/hVL3 is shown in FIG. 2.

Example 3

Binding of the Humanized Antibody Variants to Different Cells Expressing EGFR

Using IgG antibodies comprising these humanized heavy and light chain variable regions in different combinations, FACS assays with HT-29 cells, LS 174.T cells or DU145 cells were performed. The binding of selected antibody variants are shown in FIGS. 3 to 7. It was demonstrated that the humanized antibodies, in particular the humanized antibody variant VH3/VL3, have antigen binding properties comparable to those of the chimeric antibody from which they are derived. Furthermore, also VH7 and VH8 antibody variants showed good binding to these cells.

Example 4

Circulation Half-Life of the Selected Humanized Antibody Variant

The half-life of the humanized antibody variant VH3/VL3 in the circulation of mammals was compared to the half-life of the chimeric antibody. Both antibodies were produced in the same human myeloid leukemia cell line having a high sialylation activity. 10 μg antibody/mouse were injected into mice and the relative amount of antibody recovered after the indicated time was detected. Tests were done in triplicate. The results are shown in FIG. 8. It is demonstrated that the selected humanized antibody variant has an identical circulation half-life compared to the chimeric antibody.

In a further pharmacokinetic assay, the circulation half-life of the chimeric Cetuximab variant either expressed in a human myeloid leukemia cell line having a high sialylation activity (chimera sial. +) or expressed in the mouse myeloid cell line SP2/0 having a low sialylation activity (chimera sial. −) was tested in an in vivo cynomolgus monkey assay. The results are shown in FIG. 9. Therein, it is demonstrated that antibodies having a high degree of sialylation at the Fab part have a much higher circulation half-life than antibodies having a low degree of sialylation at the Fab part:

TABLE 2

|  | $C_{max}$ [μg/mL] | $t_{1/2}$ [h] | $AUC_{0-\infty}$ [μg * h/mL] |
| --- | --- | --- | --- |
| chimera sial.+ | 664 ± 53 | 110 ± 28 | 74,600 ± 18,400 |
| chimera sial.− | 589 ± 58 | 68 ± 7 | 46,400 ± 2,800 |

Thus, by increasing the amount of sialic acid in the Fab glycosylation, the circulation half-life of Cetuximab was considerably increased.

In summary, it was demonstrated that the humanized Cetuximab version not having a Fab glycosylation site and the chimeric Cetuximab version having a Fab glycosylation site and a high sialylation degree at the Fab part have a similar circulation half-life, whereas said highly sialylated chimeric Cetuximab version has a higher circulation half-life in monkeys than a lowly sialylated chimeric Cetuximab version. Therefore, the humanized Cetuximab version not having a Fab glycosylation site also will have a higher circulation half-life in primates than a Fab-glycosylated chimeric Cetuximab having a low sialylation degree. Thus, eliminating the Fab glycosylation site in the humanized Cetuximab enhanced the circulation half-life in primates compared to non-high sialylated, Fab-glycosylated chimeric Cetuximab versions. Hence, the humanized Cetuximab version is independent of the sialylation activity of its production cell line, in particular if a favorable high circulation half-life is desired.

Example 5

Binding of the Selected Humanized Antibody Variant to EGF Receptor by Surface Plasmon Resonance Binding of the selected humanized antibody variant hVH/hVL3 to its antigen EGFR was determined by surface plasmon resonance measurements and compared to the binding of the chimeric human/mouse antibody. EGF receptor extracellular domain was covalently immobilized on a Biacore® CM5 chip. The antibodies were diluted to 50 μg/mL in HBS-EP (10 mM Hepes, pH 7.4, 150 mM NaCl, 3 mM EDTA, 0.005% Polysorbate 20). At a flow of 10 μL/min 30 μL antibody dilution was injected. After injection, the antibody was allowed to dissociate for about 4.5 min. Regeneration of the surface was achieved by injection of 10 mM glycine pH 2 to 2.5. The response units were blank subtracted. The sensorgrams were normalized to maximal response and are shown in FIG. 10. Very strong and comparable binding was observed for the humanized and the chimeric anti-EGFR antibodies. In particular, the humanized variant showed a slightly higher association rate while the chimeric antibody had a slightly lower dissociation rate.

Example 6

Binding of the Selected Humanized Antibody Variant to the Fc Gamma IIIA Receptor Antibody binding to the Fc gamma IIIA Receptor was analyzed by ELISA. The receptor was immobilized in a 96-well plate. Individual samples of the humanized variant hVH3/hVL3 or the chimeric variant were incubated, washed and the bound antibodies were detected by a horseradish peroxidase conjugated F(ab)2-anti human F(ab)2 antibody. Signals were plotted against the sample concentrations resulting in sigmoidal dose response curves. Very comparable binding curves were measured for both antibodies, as shown in FIG. 11. As a result, the humanized antibody and the chimeric antibody bind with comparable efficacy to the Fc gamma IIIA Receptor.

Example 7

Antibody-Dependent Cell Cytotoxicity of the Selected Humanized Antibody Variant VH3/VL3

Antibody-dependent cellular cytotoxicity was analyzed in a europium release assay. The EGFR-positive target cell line A549 was loaded with europium ($Eu^{3+}$) by electroporation and incubated with thawed primary human peripheral blood mononuclear cells which had previously been stored in liquid nitrogen (PBMCs, effector cells) at an E:T ratio of 80:1 in the presence of the humanized variant hVH3/hVL3 or the chimeric variant of the anti-EGFR antibody obtained from human expression cell lines, the chimeric variant expressed in murine cells, or human control antibodies at different concentrations for 5 hours. Europium release to the supernatant (indicating antibody mediated cell death) was quantified using a fluorescence plate reader Infinite F200 (Tecan Austria GmbH). Maximal release was achieved by incubation of target cells with triton-X-100 and spontaneous release was measured in samples containing only target cells but no antibody and PBMC's. Specific cytotoxicity was calculated as:

% specific lysis=(experimental release−spontaneous release)/(maximal release−spontaneous release)× 100.

Dose response curves were calculated using GraphPad Prism 5. Results are given in FIG. 12. On A549 cells, the humanized and chimeric variants obtained from human cell lines mediated comparable and strong ADCC activity of the human PBMCs in a concentration-dependent manner. Due to the glycosylation differences, ADCC activity of the chimeric variant expressed in murine cells was reduced.

Example 8

Apoptosis Induction by the Selected Humanized Antibody Variant VH3/VL3

Induction of apoptosis is a further mechanism by which antibodies can mediate anti-tumor activity. While direct induction of apoptosis by monomeric antibodies is often ineffective, cross-linking of the antibody by anti-human immunoglobulin antibodies or protein G evokes this mechanism of action. In vivo, cross-linking of the antibody can be induced by Fc-receptor-bearing cells.

The induction of apoptosis by the humanized variant hVH3/hVL3 or the chimeric variant of the anti-EGFR antibody obtained from human expression cell lines, or the chimeric variant expressed in murine cells after cross-linking with anti-human immunoglobulin antibodies was analyzed on the tumor cell line A431. As a marker for induction of apoptosis, the activation of caspase-3 was analyzed using the BD PE Active Caspase-3 Apoptosis Kit. Caspase-3, a cystein protease, is a key protease that is activated during the early stages of apoptosis. It is synthesized as an inactive pro-enzyme of 32 kDa that is processed in cells undergoing apoptosis. The processed form consists of two subunits (17 kDa and 12 kDa) which associate to form the active caspase. Active caspase-3 proteolytically cleaves and activates other caspases as well as targets in the cytoplasm and in the nucleus, thereby promoting apoptosis. Using the BD PE Active Caspase-3 Apoptosis Kit, apoptotic cells are stained using an antibody specific for the active form of caspase-3 that does not recognize the inactive pro-enzyme form of caspase-3.

A431 cells were cultured in serum free medium for 24 h prior to the assay. Cells were seeded into 48 well plates and incubated at 37° C. in a $CO_2$ incubator for 24 h. The indicated antibody or hIgG1 as a negative control and anti-human immunoglobulin antibodies at a final concentration of 1 μg/ml were added. The plates were incubated for 4 to 48 h at 37° C. in a $CO_2$ incubator.

Cells were harvested, permeabilized, fixed and stained for active caspase-3 according to manufacturer's protocol. As a control, staining was performed with a isotype control antibody in parallel. Active caspase-3-positive (apoptotic) cells were analyzed by flow cytometry at a BD FACS Canto II flow cytometer using BD FACSDiva™ Software.

After cross-linking by anti-human IgG antibodies, the humanized and both chimeric versions of the anti-EGFR antibody induced apoptosis in A431 cells (see FIG. 13).

Example 9

Inhibition of Proliferation by the Selected Humanized Antibody Variant VH3/VL3

The effects of the humanized variant hVH3/hVL3 or the chimeric variant of the anti-EGFR antibody obtained from human expression cell lines, or the chimeric variant expressed in murine cells on the proliferation of EGFR-positive A431 cells (human epidermoid carcinoma cell line of the vulva) was measured in an MTT assay with different concentrations (0.1-100 μg/ml) of the respective antibody. The MTT assay is a non-radioactive assay based on the cleavage of the soluble yellow tetrazolium salt MTT (3-[4,5-Dimethylthiazol-2-yl]-2,5-diphenyltetrazolium bromide; Thiazolyl Blue) by mitochondrial dehydrogenases of viable cells. This results in the formation of a purple formazan, which can be measured in an ELISA reader at 570 nm. The absorption signal is a direct measure of viable cells in the culture.

A431 cells were grown for 2 days in 96-well flat bottom plates. The indicated antibody or hIgG1 as a negative control were added. The plates were incubated for another 4 days at 37° C. in a humidified $CO_2$ incubator. Supernatant was completely removed and MTT was added. Cells were incubated for 2 h with MTT at 37° C. in a humidified $CO_2$ incubator. The supernatant was removed and cells were lysed using a lysis buffer containing HCl and 2-propanol for 1 h at room temperature in the dark. Absorption at 570 nm/630 nm was measured in a plate reader Infinite F200 (Tecan Austria GmbH).

The humanized and both chimeric versions of the anti-EGFR antibody showed comparable inhibition of A431 proliferation after 4 days (see FIG. 14).

Example 10

Anti-Tumor Activity of the Selected Humanized Antibody Variant in Animal Model For comparison of the humanized antibody with the chimeric antibody, A431 epidermal vulva carcinoma cells were used to set up a mouse xenograft model. This cell line is expressing the EGFR protein highly.

The humanized antibody variant hVH3/hVL3 and the chimeric antibody (N=8f/group) were administered intravenously twice weekly for 3 weeks at dose levels of 5 mg/kg and 50 mg/kg. The application volume was 10 μl/g body weight for both antibody formulations. Xenografted mice were treated at the indicated dosage level when tumors reached palpable size. Both antibodies, the humanized as well as the chimeric antibody, inhibit tumor growth dose-dependently compared to PBS treated animals. No significant difference between the relative tumor volume in group treated with the humanized antibody and group treated with the chimeric antibody was found.

All animals survived until the scheduled study end. No significant changes in the body weight of the animals were observed indicating that no major toxicity occurred in the treated animals.

The invention claimed is:

1. A humanized antibody or a fragment thereof which is capable of binding to an epidermal growth factor receptor (EGFR) and which comprises:
   (a) a heavy chain variable region, comprising
      (i) the amino acid sequence of SEQ ID NO: 20, or
      (ii) an amino acid sequence which shares an identity of at least 90% with the amino acid sequence of SEQ ID NO: 20 and wherein VH CDR1 has the amino acid sequence of SEQ ID NO: 1, VH CDR2 has the amino acid sequence of SEQ ID NO: 2, and VH CDR3 has the amino acid sequence of SEQ ID NO: 3; and
   (b) a light chain variable region, comprising
      (i) the amino acid sequence of SEQ ID NO: 29, or
      (ii) an amino acid sequence which shares an identity of at least 90% with the amino acid sequence of SEQ ID NO: 29 and wherein VL CDR1 has the amino acid sequence of SEQ ID NO: 5, VL CDR2 has the amino acid sequence of SEQ ID NO: 6, and VL CDR3 has the amino acid sequence of SEQ ID NO: 7;
   and wherein the antibody or fragment thereof binds to EGFR with an affinity having a dissociation constant which is at most 10-fold higher than that of a reference antibody comprising a heavy chain variable region with the amino acid sequence of SEQ ID NO: 4 and a light chain variable region with the amino acid sequence of SEQ ID NO: 8.

2. The humanized antibody or fragment thereof according to claim 1, wherein the heavy chain variable region comprises the amino acid sequence of SEQ ID NO: 20 and the light chain variable region comprises the amino acid sequence of SEQ ID NO: 29.

3. The antibody or fragment thereof according to claim 1, wherein the antibody comprises:
   (a) a heavy chain variable region which:
      (i) comprises an amino acid sequences which shares an identity of at least 90% with the amino acid sequence of SEQ ID NO: 20,
      (ii) comprises a VH CDR1 amino acid sequence set forth in SEQ ID NO: 1, a VH CDR2 amino acid sequence set forth in SEQ ID NO: 2, and a VH CDR3 amino acid sequence set forth in SEQ ID NO: 3, and
      (iii) comprises an amino acid sequence selected from the group consisting of SEQ ID NOs:19, 20, 22, 23; and (b) a light chain variable region which:
   (i) comprises an amino acid sequence which shares an identity of at least 90% with the amino acid sequence of SEQ ID NO: 29
   (ii) comprises a VL CDR1 amino acid sequence set forth in SEQ ID NO: 5, a VL CDR2 amino acid sequence set forth in SEQ ID NO: 6, and a VL CDR3 amino acid sequence set forth in SEQ ID NO: 7; and
   (iii) comprises an amino acid sequence selected from the group consisting of SEQ ID NOs: 27, 28, 29, and 30.

4. The humanized antibody or fragment thereof according to claim 1, which does not have a glycosylation site in its heavy chain variable region.

5. The humanized antibody or fragment thereof according to claim 4, having the following characteristics:
   (a) it does not have a glycosylation site in its Fab part;
   (b) it does not have an asparagine residue at amino acid position 85 of the heavy chain variable region according to the Kabat numbering; and/or
   it does not have a serine or threonine at position 87 of the heavy chain variable region according to the Kabat numbering; and
   (c) it has a higher circulation half-life in primates than a corresponding antibody having a glycosylation site in the Fab part.

6. The humanized antibody or fragment thereof according to claim 1, having a glycosylation pattern which has one or more of the following characteristics:
   (a) it is a human glycosylation pattern;
   (b) it enhances its binding affinity to its specific epitope, its binding affinity to one or more of its downstream receptors, its complement dependent cytotoxicity (CDC), and/or its antibody-dependent cell-mediated cytotoxicity (ADCC);
   (c) it is a glycosylation pattern as obtained when expressing the antibody or fragment thereof in a cell line selected from the group consisting of K562, KG1, MUTZ-3, NM-F9, NM-D4, NM-H9D8, NM-H9D8-E6, NM H9D8-E6Q12, and GT-2X.

7. A nucleic acid encoding the antibody or fragment thereof according to claim 1.

8. An expression cassette or vector comprising the nucleic acid according to claim 7 and a promoter operatively connected with said nucleic acid.

9. An isolated host cell comprising the expression cassette or vector according to claim 8.

10. A conjugate comprising the antibody or fragment thereof according to claim 1 conjugated to a further agent.

11. A composition comprising the conjugate according to claim 10 and one or more components selected from the group consisting of solvents, diluents, and excipients.

12. A composition comprising the antibody or fragment thereof according to claim 1 and one or more components selected from the group consisting of solvents, diluents, and excipients.

13. A method for treatment of cancer in a patient, comprising administering to the patient a therapeutically effective amount of the antibody or fragment, thereof according to claim 1, thereby treating cancer.

14. The method according to claim 13, wherein the cancer is selected from the group consisting of colorectal cancer, head and neck cancer, and lung cancer.

15. The method according to claim 13, wherein the treatment of cancer further comprises the administration of a cytotoxic agent.

16. The method according to claim 15, wherein the cytotoxic agent is selected from the group consisting of doxorubicin, taxol and cisplatin.

17. A humanized antibody or a fragment thereof which is capable of binding to an epidermal growth factor receptor (EGFR) and comprises a heavy chain variable region comprising the amino acid sequence of SEQ ID NO:20 and a light chain variable region comprising the amino acid sequence of SEQ IN NO:29.

18. A humanized antibody or a fragment thereof which is capable of binding to an epidermal growth factor receptor (EGFR) comprising heavy and light chain variable regions, wherein the heavy chain variable region comprises the amino acid sequence of SEQ ID NO:20.

19. A humanized antibody or a fragment thereof which is capable of binding to an epidermal growth factor receptor (EGFR) comprising heavy and light chain variable regions, wherein the light chain variable region comprises the amino acid sequence of SEQ ID NO:29.

* * * * *

SEQUENCE LISTING

```
<160> NUMBER OF SEQ ID NOS: 34

<210> SEQ ID NO 1
<211> LENGTH: 5
<212> TYPE: PRT
<213> ORGANISM: Artificial
<220> FEATURE:
<223> OTHER INFORMATION: CDRH1

<400> SEQUENCE: 1
```

```
Asn Tyr Gly Val His
1               5

<210> SEQ ID NO 2
<211> LENGTH: 16
<212> TYPE: PRT
<213> ORGANISM: Artificial
<220> FEATURE:
<223> OTHER INFORMATION: CDRH2

<400> SEQUENCE: 2

Val Ile Trp Ser Gly Gly Asn Thr Asp Tyr Asn Thr Pro Phe Thr Ser
1               5                   10                  15

<210> SEQ ID NO 3
<211> LENGTH: 11
<212> TYPE: PRT
<213> ORGANISM: Artificial
<220> FEATURE:
<223> OTHER INFORMATION: CDRH3

<400> SEQUENCE: 3

Ala Leu Thr Tyr Tyr Asp Tyr Glu Phe Ala Tyr
1               5                   10

<210> SEQ ID NO 4
<211> LENGTH: 119
<212> TYPE: PRT
<213> ORGANISM: Artificial
<220> FEATURE:
<223> OTHER INFORMATION: heavy chain variable region

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 5
<211> LENGTH: 11
<212> TYPE: PRT
<213> ORGANISM: Artificial
<220> FEATURE:
<223> OTHER INFORMATION: CDRL1

<400> SEQUENCE: 5

Arg Ala Ser Gln Ser Ile Gly Thr Asn Ile His
1               5                   10

<210> SEQ ID NO 6
<211> LENGTH: 7
```

```
<212> TYPE: PRT
<213> ORGANISM: Artificial
<220> FEATURE:
<223> OTHER INFORMATION: CDRL2

<400> SEQUENCE: 6

Tyr Ala Ser Glu Ser Ile Ser
1               5

<210> SEQ ID NO 7
<211> LENGTH: 9
<212> TYPE: PRT
<213> ORGANISM: Artificial
<220> FEATURE:
<223> OTHER INFORMATION: CDRL3

<400> SEQUENCE: 7

Gln Gln Asn Asn Asn Trp Pro Thr Thr
1               5

<210> SEQ ID NO 8
<211> LENGTH: 108
<212> TYPE: PRT
<213> ORGANISM: Artificial
<220> FEATURE:
<223> OTHER INFORMATION: light chain variable region

<400> SEQUENCE: 8

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 9
<211> LENGTH: 30
<212> TYPE: PRT
<213> ORGANISM: Artificial
<220> FEATURE:
<223> OTHER INFORMATION: FR H1
<220> FEATURE:
<221> NAME/KEY: MISC_FEATURE
<222> LOCATION: (6)..(6)
<223> OTHER INFORMATION: Xaa is Glu or Gln
<220> FEATURE:
<221> NAME/KEY: MISC_FEATURE
<222> LOCATION: (27)..(27)
<223> OTHER INFORMATION: Xaa is Gly or Phe

<400> SEQUENCE: 9

Gln Val Gln Leu Gln Xaa Ser Gly Pro Gly Leu Val Lys Pro Ser Glu
1               5                   10                  15

Thr Leu Ser Leu Thr Cys Thr Val Ser Gly Xaa Ser Ile Ser
            20                  25                  30
```

```
<210> SEQ ID NO 10
<211> LENGTH: 14
<212> TYPE: PRT
<213> ORGANISM: Artificial
<220> FEATURE:
<223> OTHER INFORMATION: FR H2
<220> FEATURE:
<221> NAME/KEY: MISC_FEATURE
<222> LOCATION: (5)..(5)
<223> OTHER INFORMATION: Xaa is Pro or Ser

<400> SEQUENCE: 10

Trp Ile Arg Gln Xaa Pro Gly Lys Gly Leu Glu Trp Ile Gly
1               5                   10

<210> SEQ ID NO 11
<211> LENGTH: 32
<212> TYPE: PRT
<213> ORGANISM: Artificial
<220> FEATURE:
<223> OTHER INFORMATION: FR H3
<220> FEATURE:
<221> NAME/KEY: MISC_FEATURE
<222> LOCATION: (5)..(5)
<223> OTHER INFORMATION: Xaa is Ser or Asn
<220> FEATURE:
<221> NAME/KEY: MISC_FEATURE
<222> LOCATION: (6)..(6)
<223> OTHER INFORMATION: Xaa is Val or Lys
<220> FEATURE:
<221> NAME/KEY: MISC_FEATURE
<222> LOCATION: (8)..(8)
<223> OTHER INFORMATION: Xaa is Thr or Asn
<220> FEATURE:
<221> NAME/KEY: MISC_FEATURE
<222> LOCATION: (11)..(11)
<223> OTHER INFORMATION: Xaa is Asn or Ser
<220> FEATURE:
<221> NAME/KEY: MISC_FEATURE
<222> LOCATION: (13)..(13)
<223> OTHER INFORMATION: Xaa is Phe or Val
<220> FEATURE:
<221> NAME/KEY: MISC_FEATURE
<222> LOCATION: (15)..(15)
<223> OTHER INFORMATION: Xaa is Leu or Phe
<220> FEATURE:
<221> NAME/KEY: MISC_FEATURE
<222> LOCATION: (17)..(17)
<223> OTHER INFORMATION: Xaa is Leu or Met
<220> FEATURE:
<221> NAME/KEY: MISC_FEATURE
<222> LOCATION: (23)..(23)
<223> OTHER INFORMATION: Xaa is Ala or Asn

<400> SEQUENCE: 11

Arg Val Thr Ile Xaa Xaa Asp Xaa Ser Lys Xaa Gln Xaa Ser Xaa Lys
1               5                   10                  15

Xaa Ser Ser Val Thr Ala Xaa Asp Thr Ala Val Tyr Tyr Cys Ala Arg
            20                  25                  30

<210> SEQ ID NO 12
<211> LENGTH: 11
<212> TYPE: PRT
<213> ORGANISM: Artificial
<220> FEATURE:
<223> OTHER INFORMATION: FR H4

<400> SEQUENCE: 12

Trp Gly Gln Gly Thr Leu Val Thr Val Ser Ala
1               5                   10

<210> SEQ ID NO 13
```

```
<211> LENGTH: 23
<212> TYPE: PRT
<213> ORGANISM: Artificial
<220> FEATURE:
<223> OTHER INFORMATION: FR L1
<220> FEATURE:
<221> NAME/KEY: MISC_FEATURE
<222> LOCATION: (11)..(11)
<223> OTHER INFORMATION: Xaa is Gln or Leu
<220> FEATURE:
<221> NAME/KEY: MISC_FEATURE
<222> LOCATION: (21)..(21)
<223> OTHER INFORMATION: Xaa is Ile or Phe

<400> SEQUENCE: 13

Glu Ile Val Leu Thr Gln Ser Pro Asp Phe Xaa Ser Val Thr Pro Lys
1               5                   10                  15

Glu Lys Val Thr Xaa Thr Cys
            20

<210> SEQ ID NO 14
<211> LENGTH: 15
<212> TYPE: PRT
<213> ORGANISM: Artificial
<220> FEATURE:
<223> OTHER INFORMATION: FR L2
<220> FEATURE:
<221> NAME/KEY: MISC_FEATURE
<222> LOCATION: (11)..(11)
<223> OTHER INFORMATION: Xaa is Lys or Arg

<400> SEQUENCE: 14

Trp Tyr Gln Gln Lys Pro Asp Gln Ser Pro Xaa Leu Leu Ile Lys
1               5                   10                  15

<210> SEQ ID NO 15
<211> LENGTH: 32
<212> TYPE: PRT
<213> ORGANISM: Artificial
<220> FEATURE:
<223> OTHER INFORMATION: FR L3
<220> FEATURE:
<221> NAME/KEY: MISC_FEATURE
<222> LOCATION: (27)..(27)
<223> OTHER INFORMATION: Xaa is Ala or Ile
<220> FEATURE:
<221> NAME/KEY: MISC_FEATURE
<222> LOCATION: (29)..(29)
<223> OTHER INFORMATION: Xaa is Thr or Asp

<400> SEQUENCE: 15

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Xaa Ala Xaa Tyr Tyr Cys
            20                  25                  30

<210> SEQ ID NO 16
<211> LENGTH: 11
<212> TYPE: PRT
<213> ORGANISM: Artificial
<220> FEATURE:
<223> OTHER INFORMATION: FR L4
<220> FEATURE:
<221> NAME/KEY: MISC_FEATURE
<222> LOCATION: (3)..(3)
<223> OTHER INFORMATION: Xaa is Gln or Ala

<400> SEQUENCE: 16

Phe Gly Xaa Gly Thr Lys Leu Glu Ile Lys Arg
1               5                   10
```

```
<210> SEQ ID NO 17
<211> LENGTH: 119
<212> TYPE: PRT
<213> ORGANISM: Artificial
<220> FEATURE:
<223> OTHER INFORMATION: hVH
<220> FEATURE:
<221> NAME/KEY: MISC_FEATURE
<222> LOCATION: (6)..(6)
<223> OTHER INFORMATION: Xaa is Glu or Gln
<220> FEATURE:
<221> NAME/KEY: MISC_FEATURE
<222> LOCATION: (27)..(27)
<223> OTHER INFORMATION: Xaa is Gly or Phe
<220> FEATURE:
<221> NAME/KEY: MISC_FEATURE
<222> LOCATION: (40)..(40)
<223> OTHER INFORMATION: Xaa is Pro or Ser
<220> FEATURE:
<221> NAME/KEY: MISC_FEATURE
<222> LOCATION: (70)..(70)
<223> OTHER INFORMATION: Xaa is Ser or Asn
<220> FEATURE:
<221> NAME/KEY: MISC_FEATURE
<222> LOCATION: (71)..(71)
<223> OTHER INFORMATION: Xaa is Val or Lys
<220> FEATURE:
<221> NAME/KEY: MISC_FEATURE
<222> LOCATION: (73)..(73)
<223> OTHER INFORMATION: Xaa is Thr or Asn
<220> FEATURE:
<221> NAME/KEY: MISC_FEATURE
<222> LOCATION: (76)..(76)
<223> OTHER INFORMATION: Xaa is Asn or Ser
<220> FEATURE:
<221> NAME/KEY: MISC_FEATURE
<222> LOCATION: (78)..(78)
<223> OTHER INFORMATION: Xaa is Phe or Val
<220> FEATURE:
<221> NAME/KEY: MISC_FEATURE
<222> LOCATION: (80)..(80)
<223> OTHER INFORMATION: Xaa is Leu or Phe
<220> FEATURE:
<221> NAME/KEY: MISC_FEATURE
<222> LOCATION: (82)..(82)
<223> OTHER INFORMATION: Xaa is Leu or Met
<220> FEATURE:
<221> NAME/KEY: MISC_FEATURE
<222> LOCATION: (88)..(88)
<223> OTHER INFORMATION: Xaa is Ala or Asn

<400> SEQUENCE: 17

Gln Val Gln Leu Gln Xaa Ser Gly Pro Gly Leu Val Lys Pro Ser Glu
1               5                   10                  15

Thr Leu Ser Leu Thr Cys Thr Val Ser Gly Xaa Ser Ile Ser Asn Tyr
            20                  25                  30

Gly Val His Trp Ile Arg Gln Xaa Pro Gly Lys Gly Leu Glu Trp Ile
        35                  40                  45

Gly Val Ile Trp Ser Gly Gly Asn Thr Asp Tyr Asn Thr Pro Phe Thr
    50                  55                  60

Ser Arg Val Thr Ile Xaa Asp Xaa Ser Lys Xaa Gln Xaa Ser Xaa
65                  70                  75                  80

Lys Xaa Ser Ser Val Thr Ala Xaa Asp Thr Ala Val Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115
```

-continued

```
<210> SEQ ID NO 18
<211> LENGTH: 119
<212> TYPE: PRT
<213> ORGANISM: Artificial
<220> FEATURE:
<223> OTHER INFORMATION: hVH1

<400> SEQUENCE: 18
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Gly Val His Trp Ile Arg Gln Pro Pro Gly Lys Gly Leu Glu Trp Ile
        35                  40                  45

Gly Val Ile Trp Ser Gly Gly Asn Thr Asp Tyr Asn Thr Pro Phe Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

```
<210> SEQ ID NO 19
<211> LENGTH: 119
<212> TYPE: PRT
<213> ORGANISM: Artificial
<220> FEATURE:
<223> OTHER INFORMATION: hVH2

<400> SEQUENCE: 19
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Ser Asn Tyr
            20                  25                  30

Gly Val His Trp Ile Arg Gln Pro Pro Gly Lys Gly Leu Glu Trp Ile
        35                  40                  45

Gly Val Ile Trp Ser Gly Gly Asn Thr Asp Tyr Asn Thr Pro Phe Thr
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

```
<210> SEQ ID NO 20
<211> LENGTH: 119
<212> TYPE: PRT
<213> ORGANISM: Artificial
<220> FEATURE:
<223> OTHER INFORMATION: hVH3

<400> SEQUENCE: 20
```

Gln Val Gln Leu Gln Glu Ser Gly Pro Gly Leu Val Lys Pro Ser Glu

-continued

```
1               5                   10                  15
Thr Leu Ser Leu Thr Cys Thr Val Ser Gly Phe Ser Ile Ser Asn Tyr
            20                  25                  30

Gly Val His Trp Ile Arg Gln Ser Pro Gly Lys Gly Leu Glu Trp Ile
            35                  40                  45

Gly Val Ile Trp Ser Gly Gly Asn Thr Asp Tyr Asn Thr Pro Phe Thr
            50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
            115
```

<210> SEQ ID NO 21
<211> LENGTH: 119
<212> TYPE: PRT
<213> ORGANISM: Artificial
<220> FEATURE:
<223> OTHER INFORMATION: hVH4

<400> SEQUENCE: 21

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Gly Val His Trp Ile Arg Gln Pro Pro Gly Lys Gly Leu Glu Trp Ile
            35                  40                  45

Gly Val Ile Trp Ser Gly Gly Asn Thr Asp Tyr Asn Thr Pro Phe Thr
            50                  55                  60

Ser Arg Val Thr Ile Asn Lys Asp Asn Ser Lys Ser Gln Val Ser Phe
65                  70                  75                  80

Lys Met Ser Ser Val Thr Ala Ala Asp Thr Ala Val Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
            115
```

<210> SEQ ID NO 22
<211> LENGTH: 119
<212> TYPE: PRT
<213> ORGANISM: Artificial
<220> FEATURE:
<223> OTHER INFORMATION: hVH5

<400> SEQUENCE: 22

```
Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Ile Ser Asn Tyr
            20                  25                  30

Gly Val His Trp Ile Arg Gln Ser Pro Gly Lys Gly Leu Glu Trp Ile
            35                  40                  45

Gly Val Ile Trp Ser Gly Gly Asn Thr Asp Tyr Asn Thr Pro Phe Thr
            50                  55                  60
```

```
Ser Arg Val Thr Ile Asn Lys Asp Asn Ser Lys Ser Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
            115

<210> SEQ ID NO 23
<211> LENGTH: 119
<212> TYPE: PRT
<213> ORGANISM: Artificial
<220> FEATURE:
<223> OTHER INFORMATION: hVH6

<400> SEQUENCE: 23

Gln Val Gln Leu Gln Glu Ser Gly Pro Gly Leu Val Lys Pro Ser Glu
 1               5                   10                  15

Thr Leu Ser Leu Thr Cys Thr Val Ser Gly Phe Ser Ile Ser Asn Tyr
                 20                  25                  30

Gly Val His Trp Ile Arg Gln Ser Pro Gly Lys Gly Leu Glu Trp Ile
             35                  40                  45

Gly Val Ile Trp Ser Gly Gly Asn Thr Asp Tyr Asn Thr Pro Phe Thr
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
            115

<210> SEQ ID NO 24
<211> LENGTH: 119
<212> TYPE: PRT
<213> ORGANISM: Artificial
<220> FEATURE:
<223> OTHER INFORMATION: hVH7

<400> SEQUENCE: 24

Gln Val Gln Leu Gln Gln Ser Gly Pro Gly Leu Val Lys Pro Ser Glu
 1               5                   10                  15

Thr Leu Ser Leu Thr Cys Thr Val Ser Gly Phe Ser Ile Ser Asn Tyr
                 20                  25                  30

Gly Val His Trp Ile Arg Gln Pro Pro Gly Lys Gly Leu Glu Trp Ile
             35                  40                  45

Gly Val Ile Trp Ser Gly Gly Asn Thr Asp Tyr Asn Thr Pro Phe Thr
         50                  55                  60

Ser Arg Val Thr Ile Asn Lys Asp Asn Ser Lys Ser Gln Val Ser Phe
 65                  70                  75                  80

Lys Met Ser Ser Val Thr Ala Ala Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
            115
```

<210> SEQ ID NO 25
<211> LENGTH: 119
<212> TYPE: PRT
<213> ORGANISM: Artificial
<220> FEATURE:
<223> OTHER INFORMATION: hVH8

<400> SEQUENCE: 25

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Ile Ser Asn Tyr
            20                  25                  30

Gly Val His Trp Ile Arg Gln Ser Pro Gly Lys Gly Leu Glu Trp Ile
        35                  40                  45

Gly Val Ile Trp Ser Gly Gly Asn Thr Asp Tyr Asn Thr Pro Phe Thr
    50                  55                  60

Ser Arg Val Thr Ile Asn Lys Asp Asn Ser Lys Ser Gln Val Ser Phe
65                  70                  75                  80

Lys Met Ser Ser Val Thr Ala Ala Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 26
<211> LENGTH: 108
<212> TYPE: PRT
<213> ORGANISM: Artificial
<220> FEATURE:
<223> OTHER INFORMATION: hVL
<220> FEATURE:
<221> NAME/KEY: MISC_FEATURE
<222> LOCATION: (11)..(11)
<223> OTHER INFORMATION: Xaa is Gln or Leu
<220> FEATURE:
<221> NAME/KEY: MISC_FEATURE
<222> LOCATION: (21)..(21)
<223> OTHER INFORMATION: Xaa is Ile or Phe
<220> FEATURE:
<221> NAME/KEY: MISC_FEATURE
<222> LOCATION: (45)..(45)
<223> OTHER INFORMATION: Xaa is Lys or Arg
<220> FEATURE:
<221> NAME/KEY: MISC_FEATURE
<222> LOCATION: (83)..(83)
<223> OTHER INFORMATION: Xaa is Ala or Ile
<220> FEATURE:
<221> NAME/KEY: MISC_FEATURE
<222> LOCATION: (85)..(85)
<223> OTHER INFORMATION: Xaa is Thr or Asp
<220> FEATURE:
<221> NAME/KEY: MISC_FEATURE
<222> LOCATION: (100)..(100)
<223> OTHER INFORMATION: Xaa is Gln or Ala

<400> SEQUENCE: 26

Glu Ile Val Leu Thr Gln Ser Pro Asp Phe Xaa Ser Val Thr Pro Lys
1               5                   10                  15

Glu Lys Val Thr Xaa Thr Cys Arg Ala Ser Gln Ser Ile Gly Thr Asn
            20                  25                  30

Ile His Trp Tyr Gln Gln Lys Pro Asp Gln Ser Pro Xaa Leu Leu Ile
        35                  40                  45

Lys Tyr Ala Ser Glu Ser Ile Ser Gly Val Pro Ser Arg Phe Ser Gly

```
                50                  55                  60
Ser Gly Ser Gly Thr Asp Phe Thr Leu Thr Ile Asn Ser Leu Glu Ala
 65                  70                  75                  80

Glu Asp Xaa Ala Xaa Tyr Tyr Cys Gln Gln Asn Asn Asn Trp Pro Thr
                 85                  90                  95

Thr Phe Gly Xaa Gly Thr Lys Leu Glu Ile Lys Arg
                100                 105

<210> SEQ ID NO 27
<211> LENGTH: 108
<212> TYPE: PRT
<213> ORGANISM: Artificial
<220> FEATURE:
<223> OTHER INFORMATION: hVL1

<400> SEQUENCE: 27

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Thr Asn
                20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Asn Asn Asn Trp Pro Thr
                 85                  90                  95

Thr Phe Gly Gln Gly Thr Lys Leu Glu Ile Lys Arg
                100                 105

<210> SEQ ID NO 28
<211> LENGTH: 108
<212> TYPE: PRT
<213> ORGANISM: Artificial
<220> FEATURE:
<223> OTHER INFORMATION: hVL2

<400> SEQUENCE: 28

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Thr Asn
                20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Asp Tyr Tyr Cys Gln Gln Asn Asn Asn Trp Pro Thr
                 85                  90                  95

Thr Phe Gly Gln Gly Thr Lys Leu Glu Ile Lys Arg
                100                 105

<210> SEQ ID NO 29
<211> LENGTH: 108
<212> TYPE: PRT
<213> ORGANISM: Artificial
<220> FEATURE:
```

-continued

<223> OTHER INFORMATION: hVL3

<400> SEQUENCE: 29

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Leu Glu Ile Lys Arg
            100                 105

<210> SEQ ID NO 30
<211> LENGTH: 108
<212> TYPE: PRT
<213> ORGANISM: Artificial
<220> FEATURE:
<223> OTHER INFORMATION: hVL4

<400> SEQUENCE: 30

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Asp Tyr Tyr Cys Gln Gln Asn Asn Asn Trp Pro Thr
                85                  90                  95

Thr Phe Gly Ala Gly Thr Lys Leu Glu Ile Lys Arg
            100                 105

<210> SEQ ID NO 31
<211> LENGTH: 95
<212> TYPE: PRT
<213> ORGANISM: Homo sapiens

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Trp Ser Trp Ile Arg Gln Pro Pro Gly Lys Gly Leu Glu Trp Ile Gly
        35                  40                  45

Tyr Tyr Tyr Ser Gly Ser Thr Asn Tyr Asn Pro Ser Leu Lys Ser Arg
    50                  55                  60

Val Thr Ile Ser Val Asp Thr Ser Lys Asn Gln Phe Ser Leu Lys Leu
65                  70                  75                  80

```
Ser Ser Val Thr Ala Ala Asp Thr Ala Val Tyr Tyr Cys Ala Arg
                85                  90                  95

<210> SEQ ID NO 32
<211> LENGTH: 11
<212> TYPE: PRT
<213> ORGANISM: Homo sapiens

<400> SEQUENCE: 32

Trp Gly Gln Gly Thr Leu Val Thr Val Ser Ser
1               5                   10

<210> SEQ ID NO 33
<211> LENGTH: 95
<212> TYPE: PRT
<213> ORGANISM: Homo sapiens

<400> SEQUENCE: 33

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 34
<211> LENGTH: 10
<212> TYPE: PRT
<213> ORGANISM: Homo sapiens

<400> SEQUENCE: 34

Phe Gly Gln Gly Thr Lys Leu Glu Ile Lys
1               5                   10
```